(12) United States Patent
Chodkowski et al.

(10) Patent No.: US 10,828,451 B2
(45) Date of Patent: Nov. 10, 2020

(54) PASSIVE NOSE BRIDGE PRESSURE DISTRIBUTING INSERT

(71) Applicant: KONINKLIJKE PHILIPS N.V., Eindhoven (NL)

(72) Inventors: Lauren Patricia Chodkowski, Pittsburgh, PA (US); Jonathan Sayer Grashow, Pittsburgh, PA (US); Derrick Blake Andrews, Markleton, PA (US); Nathaniel Stephens, Pittsburgh, PA (US); Duon Alex Truong, Plum Borough, PA (US)

(73) Assignee: Koninklijke Philips N.V., Eindhoven (NL)

( * ) Notice: Subject to any disclaimer, the term of this patent is extended or adjusted under 35 U.S.C. 154(b) by 316 days.

(21) Appl. No.: 15/580,877

(22) PCT Filed: Jun. 6, 2016

(86) PCT No.: PCT/IB2016/053296
§ 371 (c)(1),
(2) Date: Dec. 8, 2017

(87) PCT Pub. No.: WO2016/203338
PCT Pub. Date: Dec. 22, 2016

(65) Prior Publication Data
US 2018/0169367 A1 Jun. 21, 2018

Related U.S. Application Data

(60) Provisional application No. 62/181,390, filed on Jun. 18, 2015.

(51) Int. Cl.
*A61M 16/06* (2006.01)

(52) U.S. Cl.
CPC ........ *A61M 16/0622* (2014.02); *A61M 16/06* (2013.01); *A61M 16/0605* (2014.02); *A61M 16/0683* (2013.01); *A61M 2210/0618* (2013.01)

(58) Field of Classification Search
CPC .......... A61M 16/0683; A61M 16/0611; A61M 2210/0618; A61M 16/06; A61M 16/0622; A61M 16/0605
See application file for complete search history.

(56) References Cited

U.S. PATENT DOCUMENTS

| 6,907,882 | B2 | 6/2005 | Ging |
| 8,235,045 | B2 | 8/2012 | Moore |

(Continued)

FOREIGN PATENT DOCUMENTS

| WO | WO2010139014 A1 | 12/2010 |
| WO | WO2011019698 A1 | 2/2011 |

(Continued)

*Primary Examiner* — Samchuan C Yao
*Assistant Examiner* — Nathan M Le
(74) *Attorney, Agent, or Firm* — Michael W. Haas

(57) ABSTRACT

A respiratory interface device, a cushion body and a cushion support assembly is provided. The respiratory interface device cushion body includes a nose bridge engagement portion structured to engage a user's nose bridge, the cushion nose bridge engagement portion movable between an un-deformed first configuration and a deformed second configuration. The cushion support assembly includes a faceplate and a pressure distributing assembly. A faceplate perimeter nose bridge portion defines a recessed tapered contour. A pressure distributing assembly includes a number of pressure distributing members. A pressure distributing member is disposed at the faceplate perimeter nose bridge portion and is structured to move between a first position, wherein the pressure distributing member maintains the cushion in the first cushion configuration, and a second (Continued)

position wherein the pressure distributing member maintains the cushion in the second cushion configuration.

9 Claims, 14 Drawing Sheets

(56) References Cited

U.S. PATENT DOCUMENTS

| | | | |
|---|---|---|---|
| 2008/0190432 A1* | 8/2008 | Blochlinger | A61M 16/06 128/205.25 |
| 2010/0319700 A1* | 12/2010 | Ng | A61M 16/06 128/206.28 |
| 2011/0146685 A1* | 6/2011 | Allan | A61M 16/06 128/205.25 |
| 2011/0247628 A1 | 10/2011 | Ho | |
| 2012/0067349 A1* | 3/2012 | Barlow | A61M 16/0633 128/205.25 |
| 2012/0080035 A1* | 4/2012 | Guney | A61M 16/06 128/205.25 |
| 2012/0222680 A1* | 9/2012 | Eves | A61M 16/0683 128/206.24 |
| 2012/0234326 A1* | 9/2012 | Mazzone | A61M 16/06 128/206.26 |
| 2013/0152918 A1* | 6/2013 | Rummery | A61M 16/00 128/201.22 |
| 2014/0048078 A1 | 2/2014 | Ahnblad | |
| 2014/0326243 A1 | 11/2014 | Znamenskiy | |
| 2015/0047640 A1* | 2/2015 | Mccaslin | A61M 16/06 128/205.25 |
| 2015/0328423 A1* | 11/2015 | Siew | A61M 16/06 128/205.25 |

FOREIGN PATENT DOCUMENTS

| | | |
|---|---|---|
| WO | WO2012177152 A1 | 12/2012 |
| WO | WO2014038959 A1 | 3/2014 |

* cited by examiner

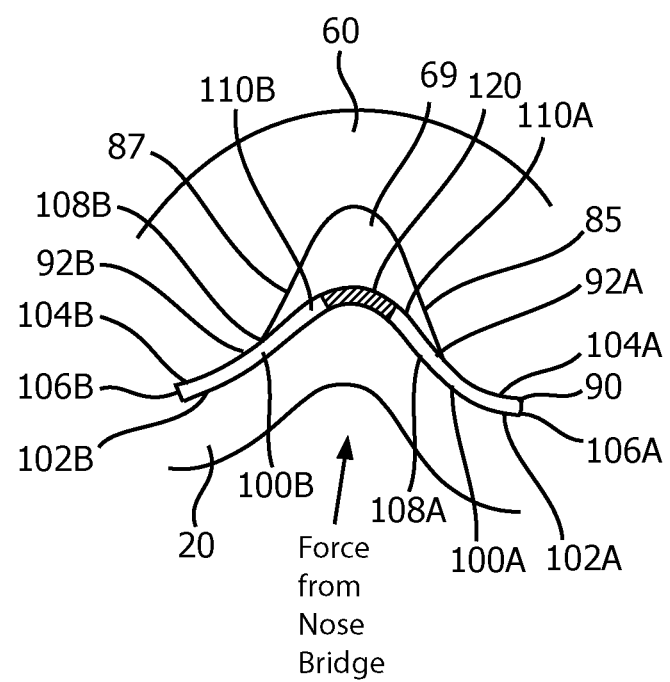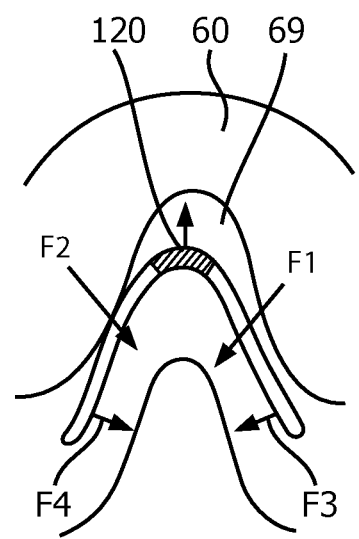
FIG. 7                                    FIG. 8

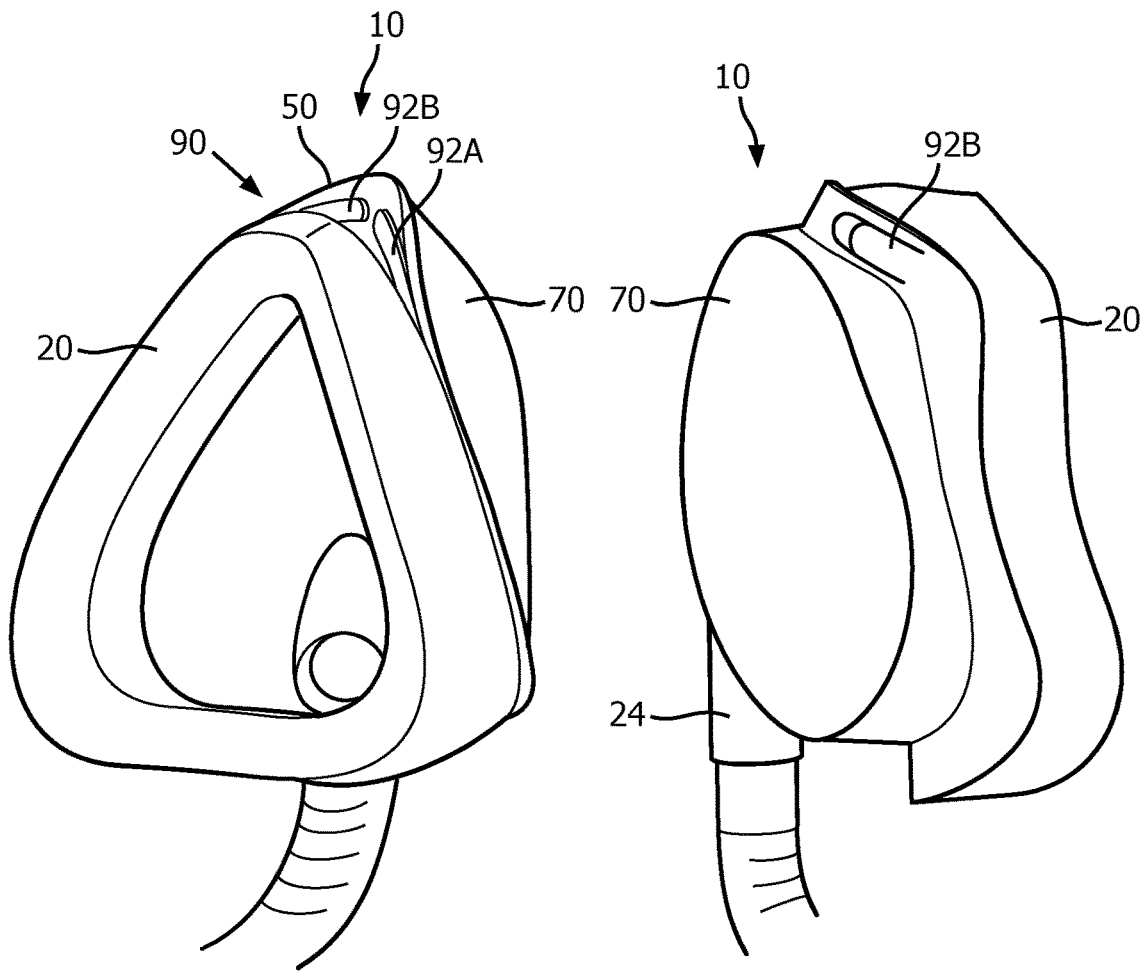
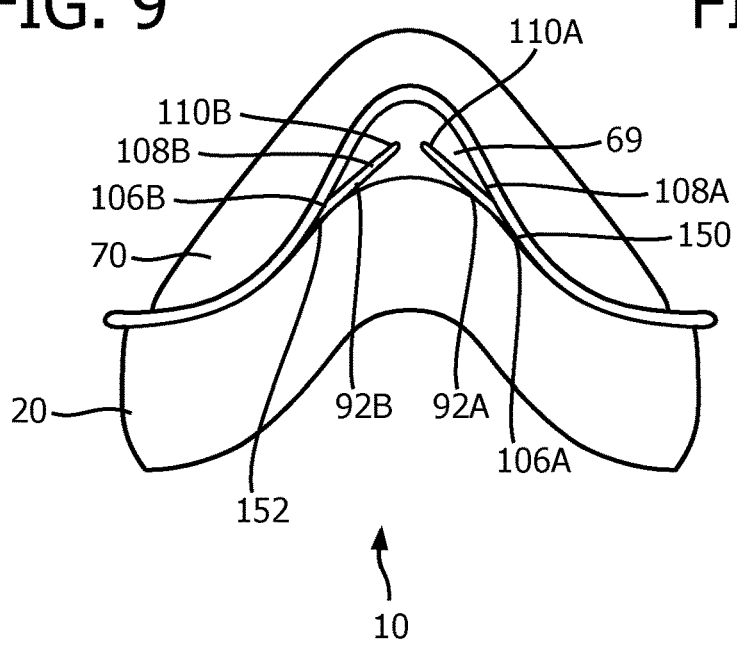
FIG. 9  FIG. 10
FIG. 11

PASSIVE NOSE BRIDGE PRESSURE DISTRIBUTING INSERT

CROSS-REFERENCE TO RELATED APPLICATIONS

This patent application claims the priority benefit under 35 U.S.C. § 371 of international patent application no. PCT/IB2016/053296, filed Jun. 6, 2016, claims the priority benefit under 35 U.S.C. § 119(e) of U.S. Provisional Application No. 62/181,390, filed on Jun. 18, 2015, the contents of which are herein incorporated by reference.

BACKGROUND OF THE INVENTION

1. Field of the Invention

The present invention pertains to patient interface devices for delivering a flow of breathing gas to a patient during, for example, respiratory therapy, and, in particular, to a patient interface device including a cushion support assembly.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient so that a flow of breathing gas can be delivered from a pressure/flow generating device to the airway of the patient. It is known to maintain such devices on the face of a wearer by a headgear having one or more straps adapted to fit over/around the patient's head. Because such patient interface devices are typically worn for an extended period of time, it is important for the headgear to maintain the mask component of the device in a tight enough seal against the patient's face without discomfort.

A typical cushion includes a resilient body that generally conforms to the user's facial contour. That is, the cushion is deformable and moves between an un-deformed first configuration and a deformed second configuration. That is, in the second configuration, the cushion generally conforms to the contour of the user's face and forms a generally continuous seal. In some locations, however, the cushion allows for gaps. That is, at certain locations such as, but not limited to, the sharp contour changes around the bridge of the nose, the cushion may gap away from the user's face.

SUMMARY OF THE INVENTION

One embodiment of the presently disclosed concept provides a respiratory interface device, a cushion body and a cushion support assembly; the cushion including a resilient body. The respiratory interface device cushion body includes a nose bridge engagement portion structured to engage a user's nose bridge, the cushion nose bridge engagement portion movable between an un-deformed first configuration and a deformed second configuration. The cushion support assembly includes a faceplate and a pressure distributing assembly. The faceplate includes a generally convex body with a perimeter. The faceplate perimeter is coupled to the cushion. The faceplate perimeter includes a nose bridge portion. The faceplate perimeter nose bridge portion defines a recessed tapered contour. The pressure distributing assembly includes a number of pressure distributing members. A pressure distributing member is disposed at the faceplate perimeter nose bridge portion and is structured to move between a first position, wherein the pressure distributing member maintains the cushion in the first cushion configuration, and a second position wherein the pressure distributing member maintains the cushion in the second cushion configuration.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 7 is a top view of a respiratory interface assembly with one embodiment of a pressure distributing assembly with the cushion in a first configuration and the pressure distributing members in a first position;

FIG. 8 is a top view of a respiratory interface assembly with one embodiment of a pressure distributing assembly with the cushion in a second configuration and the pressure distributing members in a second position;

FIG. 9 is an isometric view of a respiratory interface assembly with a second embodiment of a pressure distributing assembly;

FIG. 10 is another isometric view of a respiratory interface assembly with a second embodiment of a pressure distributing assembly;

FIG. 11 is a is a top view of a respiratory interface assembly with a second embodiment of a pressure distributing assembly;

DETAILED DESCRIPTION OF EXEMPLARY EMBODIMENTS

Figure 1:
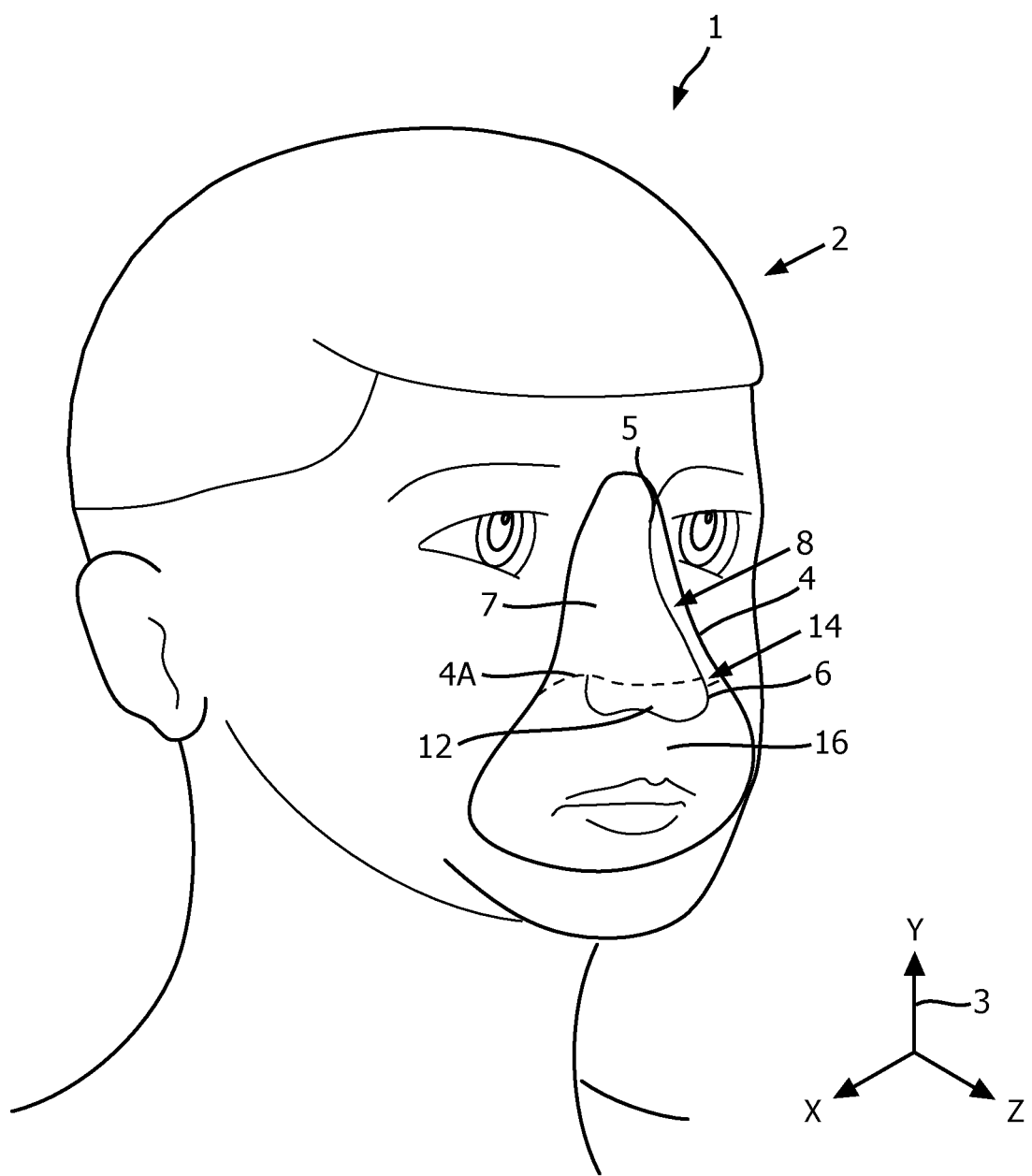
FIG. 1 is an isometric view of a user's head and face.

As used herein, the singular form of "a," "an," and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other.

It is noted that moving parts may be "directly coupled" when in one position, but not "directly coupled" when in another position. As used herein, "fixedly coupled" or "fixed" means that two components are coupled so as to move as one while maintaining a constant orientation relative to each other. Accordingly, when two elements are coupled, all portions of those elements are coupled. A description, however, of a specific portion of a first element being coupled to a second element, e.g., an axle first end being coupled to a first wheel, means that the specific portion of the first element is disposed closer to the second element than the other portions thereof.

As used herein, the phrase "removably coupled" means that one component is coupled with another component in an essentially temporary manner. That is, the two components are coupled in such a way that the joining or separation of the components is easy and would not damage the components. For example, two components secured to each other with a limited number of readily accessible fasteners are "removably coupled" whereas two components that are welded together or joined by difficult to access fasteners are not "removably coupled." A "difficult to access fastener" is one that requires the removal of one or more other components prior to accessing the fastener wherein the "other component" is not an access device such as, but not limited to, a door.

As used herein, "operatively coupled" means that a number of elements or assemblies, each of which is movable between a first position and a second position, or a first configuration and a second configuration, are coupled so that as the first element moves from one position/configuration to the other, the second element moves between positions/configurations as well. It is noted that a first element may be "operatively coupled" to another without the opposite being true.

As used herein, a "coupling assembly" includes two or more couplings or coupling components. The components of a coupling or coupling assembly are generally not part of the same element or other component. As such, the components of a "coupling assembly" may not be described at the same time in the following description.

As used herein, a "coupling" or "coupling component(s)" is one or more component(s) of a coupling assembly. That is, a coupling assembly includes at least two components that are structured to be coupled together. It is understood that the components of a coupling assembly are compatible with each other. For example, in a coupling assembly, if one coupling component is a snap socket, the other coupling component is a snap plug, or, if one coupling component is a bolt, then the other coupling component is a nut.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are to fit "snugly" together. In that situation, the difference between the size of the components is even smaller whereby the amount of friction increases. If the element defining the opening and/or the component inserted into the opening are made from a deformable or compressible material, the opening may even be slightly smaller than the component being inserted into the opening. With regard to surfaces, shapes, and lines, two, or more, "corresponding" surfaces, shapes, or lines have generally the same size, shape, and contours.

As used herein, and in the phrase "[x] moves between a first position and a second position corresponding to [y] first and second positions," wherein "[x]" and "[y]" are elements or assemblies, the word "correspond" means that when element [x] is in the first position, element [y] is in the first position, and, when element [x] is in the second position, element [y] is in the second position. It is noted that "correspond" relates to the final positions and does not mean the elements must move at the same rate or simultaneously. That is, for example, a hubcap and the wheel to which it is attached rotate in a corresponding manner. Conversely, a spring biased latched member and a latch release move at different rates. Thus, as stated above, "corresponding" positions mean that the elements are in the identified first positions at the same time, and, in the identified second positions at the same time.

As used herein, the statement that two or more parts or components "engage" one another shall mean that the elements exert a force or bias against one another either directly or through one or more intermediate elements or components. Further, as used herein with regard to moving parts, a moving part may "engage" another element during the motion from one position to another and/or may "engage" another element once in the described position. Thus, it is understood that the statements, "when element A moves to element A first position, element A engages element B," and "when element A is in element A first position, element A engages element B" are equivalent statements and mean that element A either engages element B while moving to element A first position and/or element A either engages element B while in element A first position.

As used herein, "operatively engage" means "engage and move." That is, "operatively engage" when used in relation to a first component that is structured to move a movable or rotatable second component means that the first component applies a force sufficient to cause the second component to move. For example, a screwdriver may be placed into contact with a screw. When no force is applied to the screwdriver, the screwdriver is merely "coupled" to the screw. If an axial force is applied to the screwdriver, the screwdriver is pressed against the screw and "engages" the screw. However, when a rotational force is applied to the screwdriver, the screwdriver "operatively engages" the screw and causes the screw to rotate.

As used herein, the word "unitary" means a component that is created as a single piece or unit. That is, a component that includes pieces that are created separately and then coupled together as a unit is not a "unitary" component or body As used herein, "associated" means that the elements are part of the same assembly and/or operate together, or, act upon/with each other in some manner. For example, an automobile has four tires and four hub caps. While all the elements are coupled as part of the automobile, it is understood that each hubcap is "associated" with a specific tire.

As used herein, in the phrase "[x] moves between its first position and second position," or, "[y] is structured to move [x] between its first position and second position," "[x]" is the name of an element or assembly. Further, when [x] is an element or assembly that moves between a number of positions, the pronoun "its" means "[x]," i.e. the named element or assembly that precedes the pronoun "its." As employed herein, the term "number" shall mean one or an integer greater than one (i.e., a plurality). As used herein, "a generally continuous seal" may have a gap or may gap when the user moves.

As used herein, "a more complete seal" has a gap that is shorter in length than a gap of a generally continuous seal, or, is resistant to gapping when the user moves. Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically shows a user's head 1 and face 2 with a set of Cartesian axes 3. Generally, the X-axis extends side-to-side, i.e. left to right, or as used herein, "laterally." The Y-axis extends generally vertically. The Z-axis extends forward and back. Further, as used herein, the "lateral plane" is defined by the X-axis and the Y-axis, the "horizontal plane" is defined by the X-axis and the Z-axis, and the "forward plane" is defined by the Y-axis and Z-axis. As discussed below, and as used herein, a "respiratory interface device contour" is, generally, the perimeter of the area on a user's face that a respiratory interface device engages. For a nasal and oral respiratory interface device, the "respiratory interface device contour" is a loop 4 that extends around the user's nose and mouth. The respiratory interface device contour loop 4 extends over the user's nose at a location generally between the eyes. As used herein, this area is a "nose bridge" 5. The nose further includes a tip 6, located just above the nostrils.

If nose bridge 5 is used as an origin, the nose becomes wider, i.e. in the lateral plane, and protrudes more, i.e. along the Z-axis, closer to tip 6. That is, nose bridge 5 has a minimal width and a minimal protrusion. The nose becomes wider adjacent to, and protrudes more at, tip 6 of the nose. Of course, every nose is different; an individual nose may be generally narrow and flat, generally broad and protruding, generally narrow and protruding, generally broad and flat, or somewhere in between these extremes. As used herein, the general shape of a nose is defined herein as a "protruding tapered contour." That is, a "protruding tapered contour" is a shape that becomes wider in a lateral plane and extends a greater distance along the Z-axis (protrudes) the further spaced from an origin which, for a nose, is nose bridge 5. That is, a protruding tapered contour is very generally a solid having a triangular cross-sectional shape wherein the area of the triangular cross-sectional shape increases the further it is spaced from an origin. It is, however, understood that a nose includes a generally rounded contour at the centerline. Further, in this configuration, the nose includes a generally planar surface hereinafter identified as a right side 7 and a left side 8.

Figure 2:
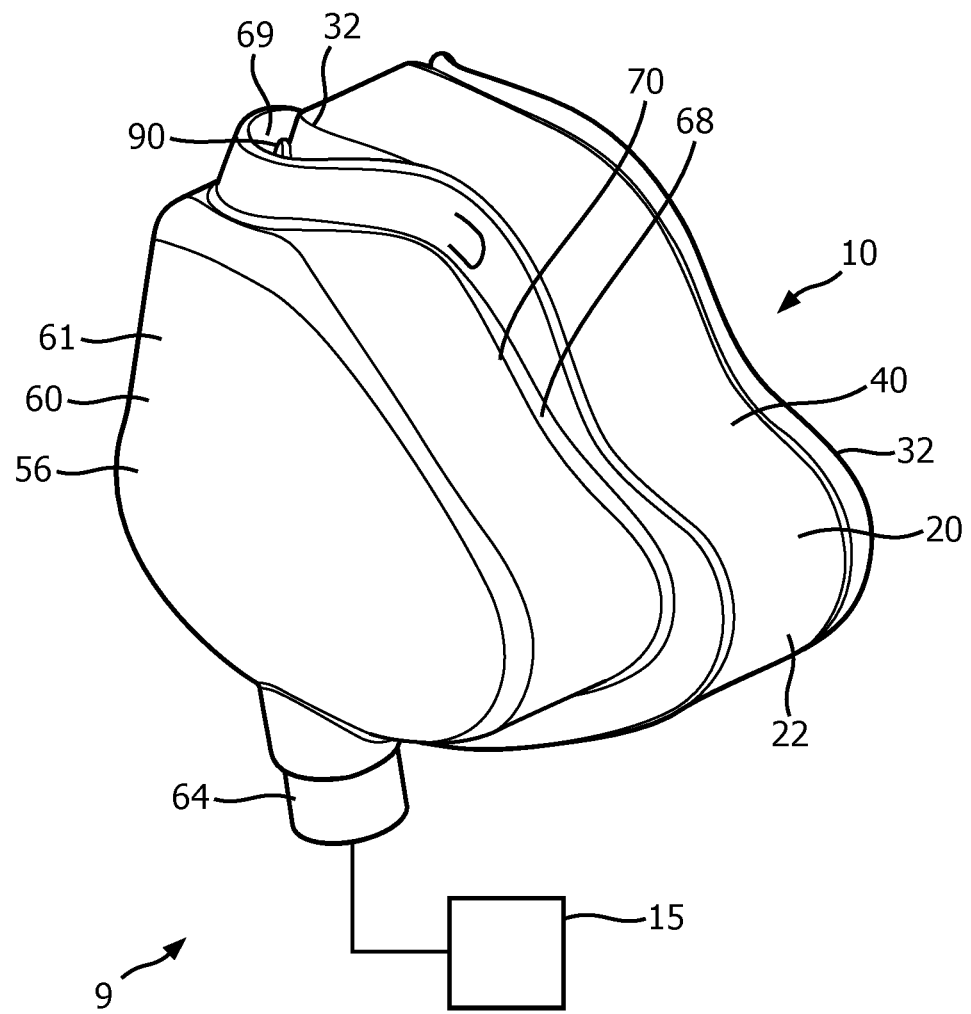
FIG. 2 is a partial schematic, isometric view of a respiratory interface assembly with one embodiment of a pressure distributing assembly.
Figure 3:
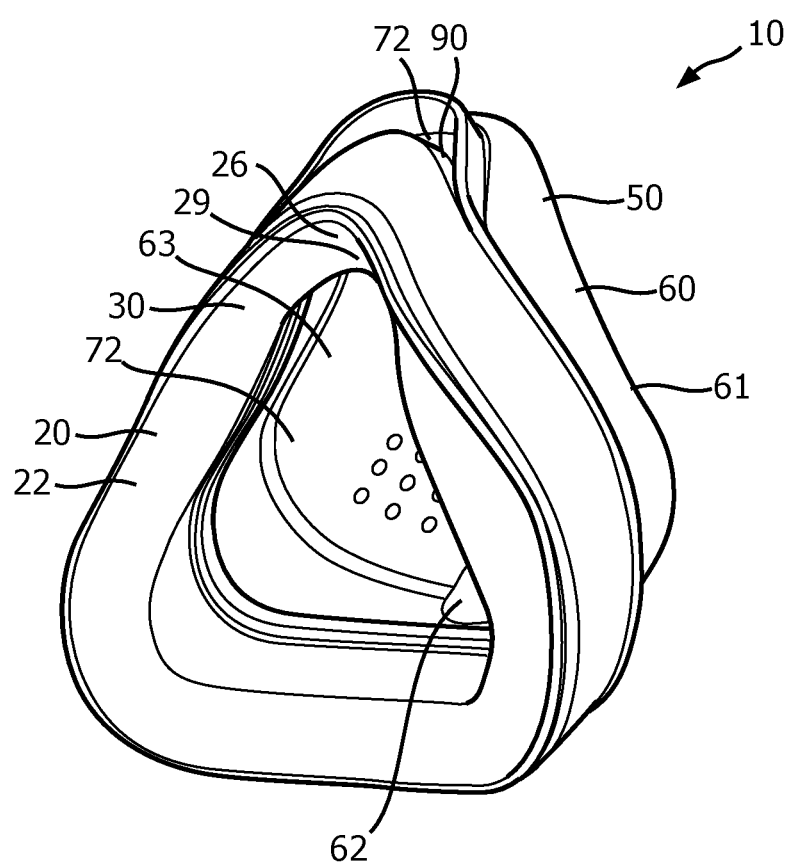
FIG. 3 is another isometric view of a respiratory interface assembly with one embodiment of a pressure distributing assembly.

FIGS. 2 and 3 schematically illustrates a respiratory interface assembly 9 according to an embodiment of the invention. Respiratory interface assembly 9 includes a respiratory interface device 10 and a support assembly such as, but not limited to straps (not shown). Respiratory interface device 10 is coupled to a pressure generating system 15 (shown schematically) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV®) device, proportional positive airway pressure (PPAP) device, C-Flex™ device, Bi-Flex™ device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

In an exemplary embodiment, shown in FIGS. 2-3, respiratory interface device 10 is a nasal and oral respiratory interface device that is structured to be disposed over a user's nose and mouth. In another exemplary embodiment, not shown, respiratory interface device 10 is a nasal respiratory interface device that is structured to be disposed over a user's nose. It is understood, however, that respiratory interface device 10 can include, without limitation, any device that provides a suitable gas flow communicating function. Thus, as used herein, the term "respiratory interface device" shall refer to any of such devices.

Respiratory interface device 10 includes a cushion 20 and a cushion support assembly 50. As is known, respiratory interface device 10 is structured to be coupled to a support assembly (not shown) such as, but not limited to a number of straps. Further, and as is known, respiratory interface device 10 is structured to be coupled to, and in fluid communication with, pressure generating system 15 via a patient circuit such as, but not limited to, a number of hoses.

In an exemplary embodiment, respiratory interface device cushion 20 (hereinafter "cushion" 20) includes a body 22. Cushion body 22 can be constructed of a wide variety of resilient materials known in the art and can include, but is not limited to, a thermoplastic or thermoelastic material, including but not limited to an elastomer such as plastic, rubber, silicone, vinyl, foam, or any combination thereof. Cushion body 22 includes a coupling component 24 and a nose bridge engagement portion 26. That is, as is known, cushion body 22 is structured to engage the user's face and provides a generally continuous seal over a respiratory interface device contour loop 4 (FIG. 1). In an exemplary embodiment, cushion body nose bridge engagement portion 26 includes a right side 28, a medial section 29, and a left side 30. As used herein, cushion body nose bridge engagement portion right side 28 (hereinafter "nose bridge engagement portion right side" 28) and cushion body nose bridge engagement portion left side 30 (hereinafter "nose bridge engagement portion left side" 30) are each a generally planar surface structured to generally correspond to the contour of a user's nose right side 7 and nose left side 8. At any local point on nose bridge engagement portion 26, the plane of nose bridge engagement portion right side 28 and nose bridge engagement portion left side 30 extends at least generally forward and toward each other. Thus, nose bridge engagement portion 26 generally corresponds to the shape of a nose, as described above.

Figure 4:
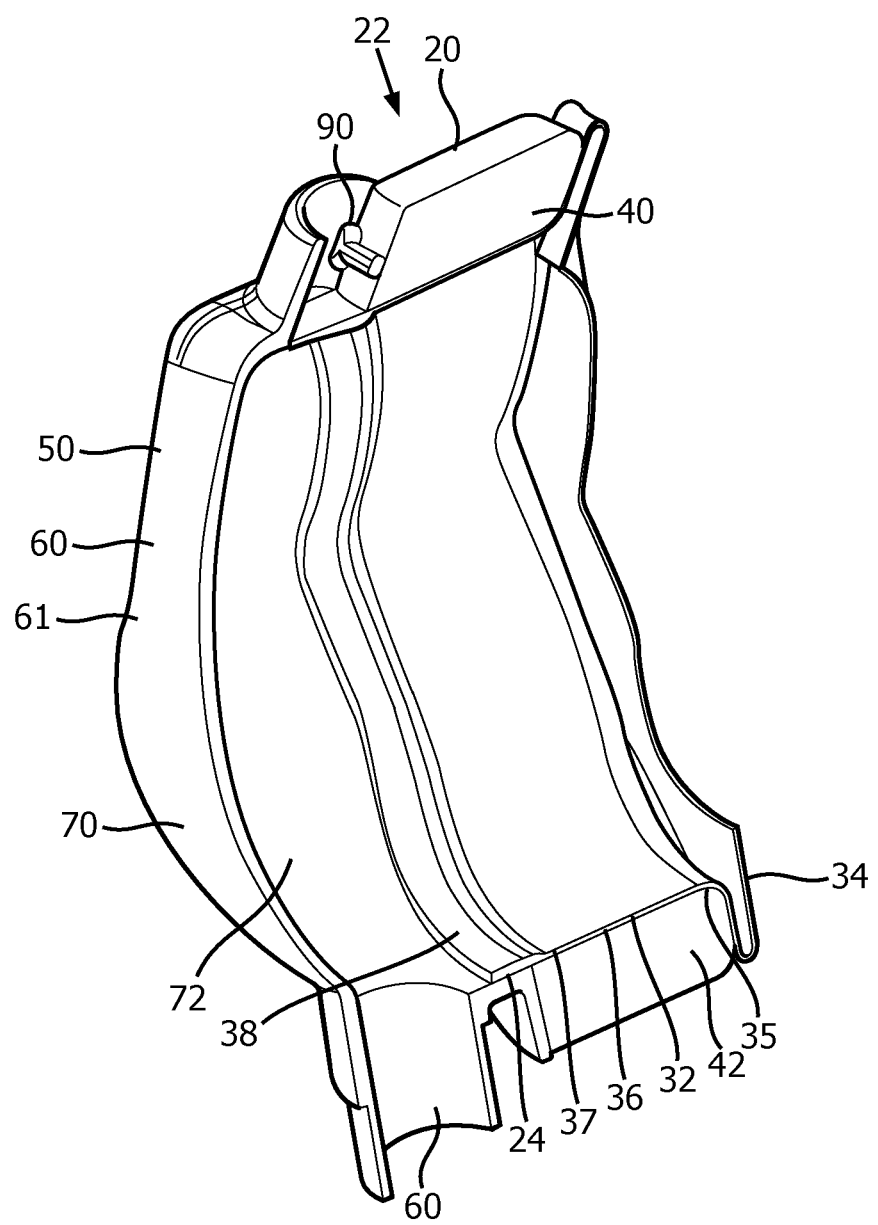
FIG. 4 is a cross-sectional view of a respiratory interface assembly with one embodiment of a pressure distributing assembly.

In an exemplary embodiment, as shown in FIG. 4, cushion body 22 is an assembly including a thin member 32 and a thick member 40, wherein "thin" and "thick" are terms relative to members 32, 40. Thin member 32 is, in an exemplary embodiment, made from a resilient elastomer such as plastic, rubber, silicone, or vinyl and is a unitary body. Thin member 32 includes a flap 34, a tubular portion 36, and a mounting 38. Tubular portion 36 includes a first end 35 and a second end 37. Flap 34 is coupled to, and in an exemplary embodiment unitary with, tubular portion first end 35. As shown, flap 34 is a "ribbon-like" body, as defined below, wherein the offset surface of the body extends, generally, parallel to the user's face. In an exemplary embodiment, flap 34 doubles-back over itself, i.e. flap 34 has a generally U-shaped cross-section. As is known, flap 34 is structured to engage a user's face and therefore defines at least cushion body nose bridge engagement portion 26. Tubular portion 36 extends in the Z-axis direction. That is, tubular portion 36 is a ribbon-like member extending about, i.e. is disposed around, the Z-axis. Mounting 38 is coupled to, and in an exemplary embodiment unitary with, tubular portion second end 37. Mounting 38 is structured to, and does, seal against faceplate 60.

Thick member 40 is, in an exemplary embodiment, made from an elastomer foam or a similar material and is a unitary body. In an exemplary embodiment, thick member 40 is resilient, but less resilient than thin member 32. Thick member 40 is, in an exemplary embodiment, also a tubular member having a ribbon-like body 42, wherein the ribbon-like body 42 is thicker than tubular portion 36. Thick member 40 is structured to fit snuggly about tubular portion 36. That is, thick member 40 has a shape that generally corresponds to the shape of tubular portion 36 and wherein the inner surface of thick member 40 extends generally parallel to X-axis substantially or snuggly corresponds to the shape of tubular portion 36.

Figure 5:
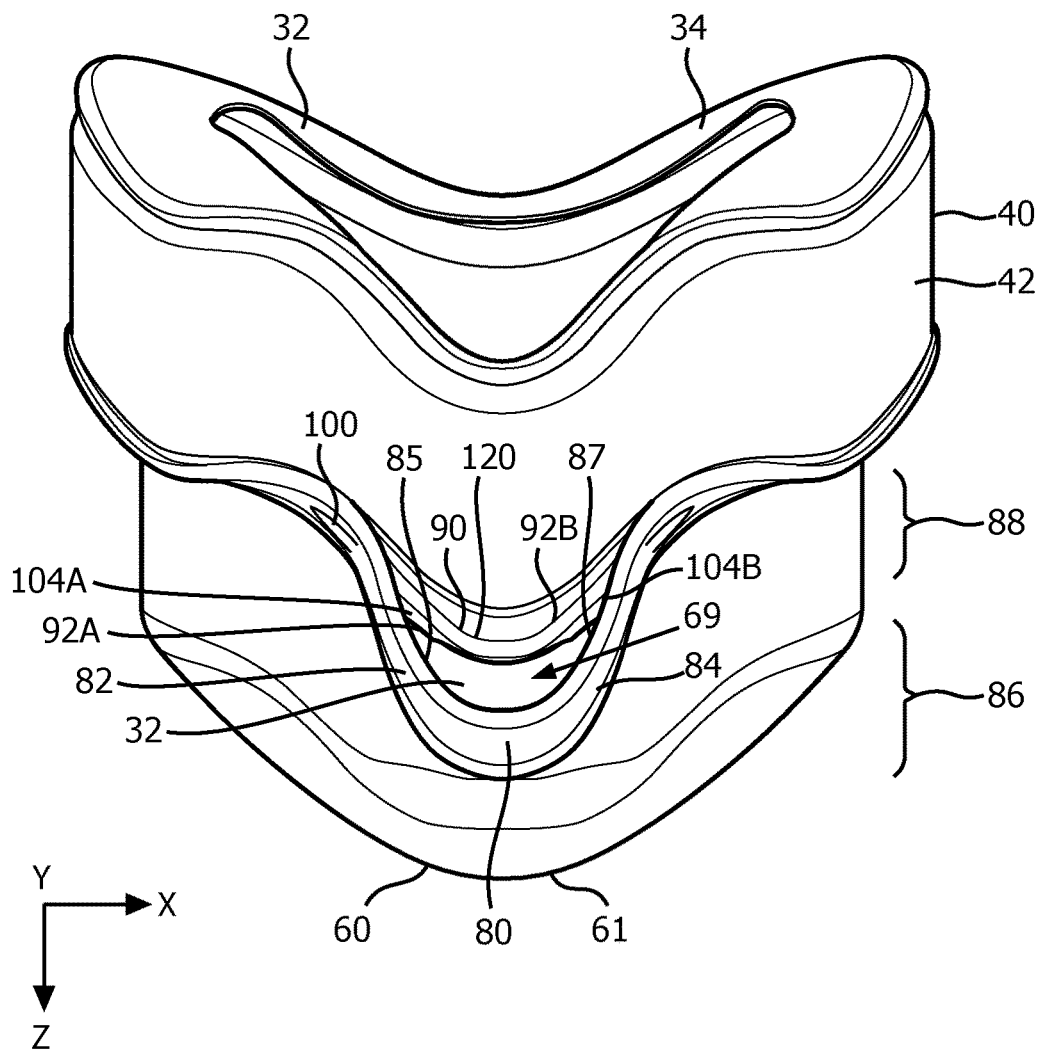
FIG. 5 is a top view of a respiratory interface assembly with one embodiment of a pressure distributing assembly.

When cushion 20 is assembled, thick member 40 is disposed about (generally encircling) tubular portion 36. Mounting 38 is structured to be, and is, sealingly coupled to faceplate 60. In this configuration, thin member 32 positions flap 34 a distance from faceplate 60, Further, flap 34 is, in this embodiment, structured to extend over a user's nose and mouth along loop 4 as described above. That is, flap 34 sealingly engages the user's face along loop 4. Further, in this configuration, an axial face of thick member 40, a surface of thick member 40 that extends generally parallel to the Y-axis, supports or engages flap 34. Thus, it is understood that deformations to thick member 40 are transferred to thin member 32. Hereinafter, the assembly described hereinabove shall be collectively identified as cushion 20 or cushion body 22, In an exemplary embodiment, as shown in FIGS. 2 and 5, cushion support assembly 50 includes faceplate 60 wherein faceplate 60 further includes a pressure distributing assembly 90. In an exemplary embodiment, cushion support assembly faceplate 60 and cushion support assembly pressure distributing assembly 90 are a unitary body. In another exemplary embodiment, cushion support assembly faceplate 60 and cushion support assembly pressure distributing assembly 90 are coupled, directly coupled, or fixed to each other. In an exemplary embodiment, cushion support assembly faceplate 60 (hereinafter "faceplate" 60) includes a substantially rigid body 61. In an exemplary embodiment, shown in FIG. 3, faceplate 60 is a single piece, i.e. a unitary body, structured to cover the user's nose and mouth. That is, respiratory interface device 10 has a peripheral contour that is, in this embodiment, structured to extend over a user's nose and mouth along loop 4 as described above. Faceplate 60 defines lower opening 62. Lower opening 62 can function as a gas inlet. Gas inlet (lower opening 62) can be coupled to a coupling device 64, such as, but not limited to, a swivel conduit, for carrying gas such as air between respiratory interface device 10 and an external gas source, such as a blower, pressure generating system 15, or any other suitable device.

It is contemplated that the external gas source can encompass, without limitation, any gas delivery or gas generation system capable of supplying gas for consumption by a user. Non-limiting examples of various gas delivery therapies can include but are not limited to continuous positive airway pressure (CPAP) therapy, auto-titration positive airway pressure therapy, and bi-level positive airway pressure (BiPAP) therapy, as noted above. The coupling device may be any of a variety of different coupling devices that could be attached, either permanently or selectively, to lower opening 62 to carry gas to or from respiratory interface device 10. Thus, a variety of coupling devices (e.g., with or without swivels on one or both ends, and with or without an exhalation system formed integral to the device) may be used.

In an exemplary embodiment, shown in FIGS. 2-5, faceplate 60, i.e. faceplate body 61, is generally convex or bowl-shaped. This shape defines an interior space 63 that accommodates a user's nose and other features when respiratory interface device 10 is in use. Faceplate 60 includes a peripheral end, identified herein as a perimeter 68, that extends about faceplate 60. In this exemplary embodiment, faceplate perimeter 68 extends generally towards the user's face when respiratory interface device 10 is in use. Faceplate 60, and faceplate perimeter 68, include an outer side 70 and an inner side 72 (relative to the interior space 63). That is, as used herein and with reference to faceplate 60, "outer" or "outwardly" means away from the interior space 63 defined by bowl-shaped faceplate 60, and, "inner" or "inwardly" means toward the interior space 63 defined by bowl-shaped faceplate 60.

In an exemplary embodiment, faceplate 60, or faceplate perimeter 68, includes a coupling component 76 structured to be coupled to cushion body coupling component 24. Thus, cushion body 22 is coupled, directly coupled, or removably coupled to faceplate 60 and generally corresponds to the shape of faceplate perimeter 68. In an exemplary embodiment, faceplate perimeter 68 also includes a nose bridge portion 80 which is that portion of faceplate perimeter 68 that extends over the user's nose bridge when respiratory interface device 10 is in use. Faceplate perimeter nose bridge portion 80 includes a right side 82, a left side 84, an upper portion 86 and a lower portion 88. Faceplate perimeter nose bridge portion upper portion 86 is generally offset, i.e.

spaced, from faceplate perimeter nose bridge portion 80. In this configuration, and when cushion 20 is coupled to faceplate 60, there is a gap 69 between faceplate perimeter nose bridge portion upper portion 86 and cushion nose bridge engagement portion 26. It is noted that, in an embodiment wherein cushion 20 includes a thin member 32 and a thick member 40, thin member 32 extends across gap 69 and is, sealingly coupled to faceplate 60, i.e. faceplate inner side 72. Accordingly, as used herein, a "gap" means a spacing between a substantial portion of cushion 20 and faceplate 60 but allows for a membrane or similar construct, such as, but not limited to thin member 32, to extend across the spacing so as to prevent gap 69 from defining a passage between the atmosphere and the interior space of faceplate 60.

Further, in an exemplary embodiment, faceplate perimeter nose bridge portion 80 defines a "recessed tapered contour." As used herein, a "recessed tapered contour" is a cavity that generally corresponds to the shape of a protruding tapered contour, i.e. a cavity that generally corresponds to the shape of a nose, except the deepest offset in the Z-axis direction is disposed at the narrowest spacing of the lateral surfaces. That is, in an exemplary embodiment, faceplate perimeter nose bridge portion 80 is substantially at the top of faceplate perimeter 68 and a "recessed tapered contour" is a contour that becomes wider the further downward the contour. The deepest, i.e. the most offset in the Z-axis direction, however, is located at the top of faceplate perimeter 68. In this configuration, faceplate perimeter 68 generally is disposed over the loop 4 shown in FIG. 1. Moreover, in this configuration cushion 20, i.e. cushion nose bridge engagement portion 26, is movable between an un-deformed first configuration and a deformed second configuration, as described below. Further, faceplate perimeter nose bridge portion 80 includes a right side 82 and a left side 84.

In an exemplary embodiment, faceplate perimeter nose bridge portion 80 defines a generally planar surface. That is, faceplate perimeter nose bridge portion 80 is a ribbon-like body. As used herein, a "ribbon-like" body includes a thin, elongated body having at least one surface that is offset and generally parallel to the body longitudinal axis. Further, at any specific point along the centerline, the offset surface has a width that extends generally perpendicular to the centerline. The body longitudinal axis may curve in three dimensions. Thus, for example, a common fabric ribbon has a generally rectangular cross-sectional shape with four surfaces that are offset and generally parallel to the longitudinal axis of the body. As used herein, the "longitudinal axis" of a "ribbon-like" body is a centerline that may curve in three dimensions. Accordingly, faceplate perimeter nose bridge portion right side 82 defines a generally planar surface 85, and, faceplate perimeter nose bridge portion left side 84 defines a generally planar surface 87.

In this exemplary embodiment, pressure distributing assembly 90 is disposed at faceplate perimeter nose bridge portion 80. Pressure distributing assembly 90 is structured to move cushion nose bridge engagement portion 26 between the first configuration and the second configuration, and to maintain cushion nose bridge engagement portion 26 in the second configuration while the respiratory interface device 10 is in use. That is, in response to a force applied to respiratory interface device 10, such as but not limited to a user tightening a respiratory interface device support assembly (i.e. straps), the user's face/nose applies a counter force to cushion 20 and cushion nose bridge engagement portion 26. This force, hereinafter and as used herein the "use force," causes cushion 20 to engage pressure distributing assembly 90 and vice-versa. It is understood that, and as used herein, "move" and "maintain" when used in reference to cushion 20 means that, during an initial application of the use force, pressure distributing assembly 90 moves/deforms cushion 20 to be in the second configuration and thereafter maintains cushion 20 in the second configuration.

In this exemplary embodiment, pressure distributing assembly 90 includes a number of movable pressure distributing members 92. That is, pressure distributing assembly pressure distributing members 92 move relative to faceplate 260. Pressure distributing assembly pressure distributing members 92, hereinafter "pressure distributing members" 92, are disposed at faceplate perimeter nose bridge portion 80 and are structured to move between a first position, wherein, when faceplate perimeter 68 is coupled to cushion 20, each pressure distributing member 92 maintains cushion 20 in the first cushion configuration, and a second position, wherein, the faceplate perimeter 68 is coupled to cushion 20, each pressure distributing member 92 maintains cushion 20 in the second cushion configuration.

In an exemplary embodiment, there are two pressure distributing members 92; a first pressure distributing member 92A disposed on faceplate perimeter nose bridge portion right side 82, and, a second pressure distributing member 92B disposed on faceplate perimeter nose bridge portion left side 84. Hereinafter, elements of first pressure distributing member 92A will include the letter "A" in the reference number, and, elements of second pressure distributing member 92B will include the letter "B" in the reference number. That is, a generic pressure distributing member 92 will be described with no letters in the reference numbers, but thereafter any reference to a specific pressure distributing member 92, or elements thereof, will include a letter as well. In the configuration described above, first pressure distributing member 92A is structured to, and does, contact and/or engage cushion nose bridge engagement portion right side 28, and, second pressure distributing member 92B is structured to, and does, contact and/or engage cushion nose bridge engagement portion left side 30. That is, the first and second pressure distributing members 92A, 92B contact and/or engage an outer side of cushion nose bridge engagement portion right/left sides 28, 30.

Figure 6:
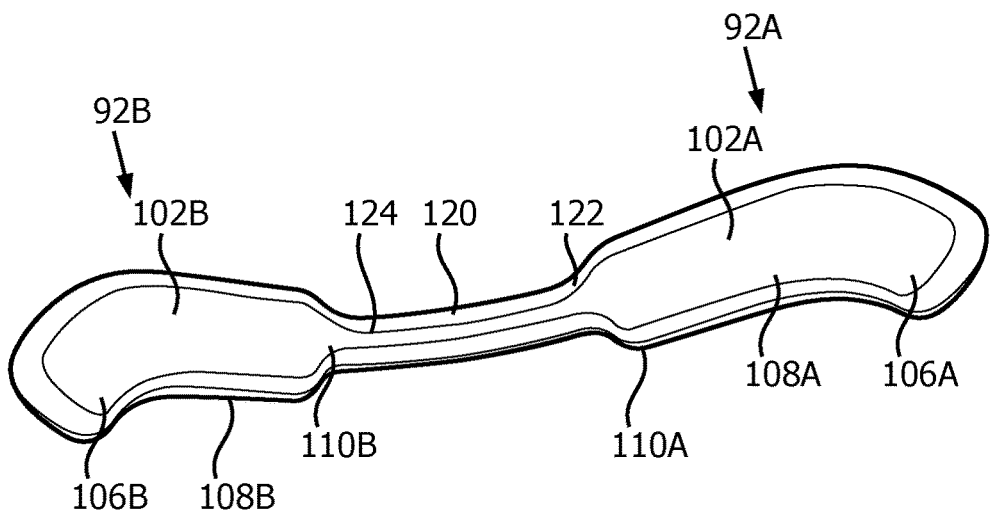
FIG. 6 is an isometric view of a unitary body pressure distributing assembly.

In an exemplary embodiment, as shown in FIG. 6, each pressure distributing member 92 includes an elongated body, or, a generally planar elongated body 100. Each pressure distributing member body 100 includes an inner side 102, an outer side 104, a first end 106, a medial portion 108, and a second end 110. In an embodiment wherein pressure distributing member body 100 is generally planar, pressure distributing member body inner side 102 and pressure distributing member body outer side 104 are the opposing broad, planar sides of pressure distributing member body 100. Further, as used herein in reference to planar pressure distributing member bodies, the "inner side" is the broad side facing the faceplate 60 cavity.

In an exemplary embodiment, shown in FIG. 6, pressure distributing assembly 90 also includes a flexure 120. As used herein, a "flexure" is a construct structured to flex. Thus, for example, flexure 120 may be made from a flexible material, or, may be rigid material with a minimal cross-sectional area. In an exemplary embodiment, flexure 120 is disposed between first pressure distributing member 92A and second pressure distributing member 92B. That is, flexure 120 includes a right end 122 and a left end 124. First pressure distributing member body second end 110A is coupled, directly coupled, or fixed to flexure right end 122. Second pressure distributing member body second end 110B is coupled, directly coupled, or fixed to flexure left end 124. In an exemplary embodiment, pressure distributing assembly 90 including flexure 120 is a unitary body. That is, first pressure distributing member body 100A, flexure 120, and second pressure distributing member body 100B are a unitary body.

In this exemplary embodiment, pressure distributing assembly 90 "freely floats" relative to faceplate 20. As used herein, "freely floats" means that a first element is generally "fixed" to a second element in that the first element generally maintains a constant orientation relative to the second element but is free to move and/or be reoriented a minimal amount. Further, when a first element includes moving parts, such as but not limited to pressure distributing assembly 90 that includes members that move between a first and second position, determination as to whether the first element generally maintains a constant orientation relative to the second element is determined relative to a portion of the first element to move a minimal amount, such as but not limited to flexure 120 disposed between two movable pressure distributing member bodies 100. It is noted that a movable coupling, such as, but not limited to a pivotal coupling, is not a coupling that allows one element to "freely float" relative to another element.

In an exemplary embodiment, pressure distributing assembly 90 is directly coupled or fixed to cushion body nose bridge engagement portion 26 and disposed between cushion 20 and faceplate 60. Thus, pressure distributing assembly 90 freely floats relative to faceplate 20. In an exemplary embodiment, the longitudinal axis of first pressure distributing member body 100A is generally disposed in one of a lateral plane, a horizontal plane, or is disposed at an angle to both a lateral plane and a horizontal plane. Similarly, in this exemplary embodiment, the longitudinal axis of second pressure distributing member body 100B is generally disposed in one of a lateral plane, a horizontal plane, or is disposed at an angle to both a lateral plane and a horizontal plane.

Further, in an exemplary embodiment, pressure distributing assembly 90 is disposed adjacent to faceplate perimeter nose bridge portion 80. As shown in FIG. 6, in this configuration, first pressure distributing member body second end 110A, flexure 120, and second pressure distributing member body second end 110B are disposed adjacent gap 69 and faceplate perimeter nose bridge portion upper portion 86. Further, first pressure distributing member body medial portion 108A and second pressure distributing member body medial portion 108B are disposed immediately adjacent faceplate perimeter nose bridge portion lower portion 88. Further, first pressure distributing member body first end 106A and second pressure distributing member body first end 106B are disposed adjacent, but not immediately adjacent, faceplate perimeter nose bridge portion lower portion 88.

In this configuration, pressure distributing assembly 90 is in a levering configuration relative to faceplate 60. That is, as shown in FIGS. 7-8, when a user positions respiratory interface device 10 for use, i.e. over the user's nose and mouth, pressure distributing assembly 90 operates as follows. When cushion 20 is coupled to faceplate 60, pressure distributing assembly 90 maintains cushion in the first configuration. As a user applies a use force, the user's nose bridge 5 engages cushion body nose bridge engagement portion 26. Generally, this engagement causes cushion body nose bridge engagement portion 26 to move into faceplate perimeter nose bridge portion 80. Then, cushion body nose bridge engagement portion 26 operatively engages first pressure distributing member body 100A and second pressure distributing member body 100B. The following also occurs. Cushion body nose bridge engagement portion 26 applies bias against first pressure distributing member body inner side 102A and second pressure distributing member body inner side 102B. Initially, first pressure distributing member body medial portion 108A and second pressure distributing member body medial portion 108B, move toward and contact faceplate 60. This contact substantially prevents first pressure distributing member body medial portion 108A and second pressure distributing member body medial portion 108B from moving toward faceplate 60, and, continued engagement of cushion body nose bridge engagement portion 26 against first and second pressure distributing member bodies 100A, 100B, cause pressure distributing member bodies 100A, 100B to move together. That is, flexure 120 flexes allowing pressure distributing member bodies 100A, 100B to move together. This motion causes first pressure distributing member body first end 106A and second pressure distributing member body first end 106B to move a greater distance relative to each other than first pressure distributing member body second end 110A and second pressure distributing member body second end 110B. It is, however, noted that first pressure distributing member body medial portion 108A and second pressure distributing member body medial portion 108B may slide over faceplate 60 after the initial contact noted above.

In this configuration, the point of contact between pressure distributing member bodies 100A, 100B and faceplate 60 acts as a sliding pivot point. That is, as used herein, a "sliding pivot point" is a construct wherein a member both slides over, and pivots about (meaning "around") an identified point or area. In this configuration, pressure distributing member bodies 100A, 100B slide over the point, or area, of contact with faceplate 60. At the same time, the lateral distance between the opposing lateral sides of faceplate perimeter nose bridge portion 80 defines a maximum separation of pressure distributing member bodies 100A, 100B at that location. Thus, pressure distributing member bodies 100A, 100B also pivot about (meaning "around") the point, or area, of contact with faceplate 60. Thus, for example, the length of pressure distributing member body 100A between first pressure distributing member body first end 106A and first pressure distributing member body medial portion 108A acts as an elongated lever arm enhancing the forces at first pressure distributing member body first end 106A.

In this configuration, first pressure distributing member body medial portion 108A, on first pressure distributing member body inner side 102A, engages cushion nose bridge engagement portion right side 28 with a first force, wherein the first force is substantially equal to the force of cushion body nose bridge engagement portion 26 against first pressure distributing member body 100A. That is, the first force is a counter-force that is substantially equal to the force of cushion body nose bridge engagement portion 26 against first pressure distributing member body 100A. Similarly, second pressure distributing member body medial portion 108B, on second pressure distributing member body inner side 102B, engages cushion nose bridge engagement portion left side 30 with a second force, wherein the second force is substantially equal to the force of cushion body nose bridge engagement portion 26 against the first pressure distributing member body 100A. First pressure distributing member body first end 106A, on first pressure distributing member body inner side 102A, engages cushion nose bridge engagement portion right side 28 with a third force. As the length of first pressure distributing member body 100A between first pressure distributing member body first end 106A and first pressure distributing member body medial portion 108A acts as an elongated lever arm, the third force is greater than the first force. Similarly, second pressure distributing member body first end 106B, on second pressure distributing member body inner side 102B, engages cushion nose bridge engagement portion left side 30 with a fourth force. The fourth force is greater than the second force. Stated very generally, pressure distributing assembly 90 pinches cushion 20 against the user's nose.

Thus, when a user positions respiratory interface device 10 for use, i.e. over the user's nose and mouth, pressure distributing assembly 90 moves from a first position, wherein pressure distributing member bodies 100A, 100B maintain cushion 20 in a first cushion configuration, and, a second position, wherein pressure distributing member bodies 100A, 100B move and maintain cushion 20 in a second cushion configuration. Further, when cushion 20 is in the second cushion configuration, cushion 20 provides a more complete seal compared to a cushion that is not supported by pressure distributing assembly 90.

In another exemplary embodiment, shown in FIGS. 9-13, first and second pressure distributing member bodies 100A, 100B are pivotally coupled to, or are unitary with, faceplate perimeter nose bridge portion 80. The names of the areas of pressure distributing member bodies 100A, 100B above are equally applicable to this embodiment and the same names and reference numbers shall be used. Thus, in this embodiment, first pressure distributing member body first end 106A is pivotally coupled, or unitary with, faceplate perimeter nose bridge portion right side 82.

In an exemplary embodiment, first pressure distributing member body first end 106A is unitary with faceplate perimeter nose bridge portion right side 82 and defines a first living hinge 150. Further in this exemplary embodiment, first living hinge 150 is a pre-flexed living hinge. That is, the longitudinal axis of first pressure distributing member body 100A is offset inwardly relative to the longitudinal axis of faceplate perimeter nose bridge portion right side planar surface 85. The left side of pressure distributing assembly 90 is, essentially, a mirror image of the right side. That is, in this exemplary embodiment, second pressure distributing member body first end 106B is pivotally coupled, or unitary with, faceplate perimeter nose bridge portion left side planar surface 87. In an exemplary embodiment, second pressure distributing member body first end 106B is unitary with faceplate perimeter nose bridge portion left side 84 and defines a second, pre-flexed living hinge 152. In this configuration, pressure distributing member bodies 100A, 100B extend into gap 69.

In this exemplary embodiment, cushion body nose bridge engagement portion 26 is disposed adjacent to, and in contact with one of first and second pressure distributing member body inner sides 102A, 102B. That is, when cushion 20 is in the cushion first configuration, cushion 20 contacts first and second pressure distributing member body first end 106A, 106B, and medial portion 108A, 108B. When a user positions respiratory interface device 10 for use, i.e. over the user's nose and mouth, pressure distributing assembly 90 operates as follows. As the user moves their nose into the respiratory interface device 10, their nose operatively engages cushion nose bridge engagement portion 26 and moves cushion nose bridge engagement portion 26 into gap 69. As cushion nose bridge engagement portion 26 moves into gap 69, cushion nose bridge engagement portion 26 engages pressure distributing member bodies 100A, 100B. Pressure distributing member bodies 100A, 100B provide a counter force to cushion nose bridge engagement portion 26 which is enhanced by the bias of pre-flexed first and second living hinges 150, 152. That is, first and second living hinges 150, 152 flex from their original positions and the force that is generated by first and second living hinges 150, 152 acts upon cushion nose bridge engagement portion 26. Stated very generally, pressure distributing assembly 90 pinches cushion 20 against the user's nose.

Another embodiment is shown in FIGS. 14-18. In this embodiment, respiratory interface device 10' is a nasal and oral cradle that is structured to be disposed generally under user's nose and over a user's mouth. That is, in this embodiment, respiratory interface device 10' is not disposed over a user's nose bridge 5. That is, the nose includes nares (openings) adjacent/under the nose tip 6. As used herein, the lateral sides of the nose outside the nares and extending to the nose tip 6 are identified as a "lower nose right side" 12 and "lower nose left side" 14. Further, as used herein, the area between the mouth and the nose is identified as the "upper lip" 16; that is, the "upper lip" includes both the thin skin area immediately adjacent the mouth as well as the thicker skin portion between the thin skin portion and the nose.

In this embodiment, a respiratory interface device cushion 220 (hereinafter "cushion" 220) and a cushion support assembly 250 are structured to cover alternate loop 4A shown in FIG. 1. That is, cushion 220 includes a body 222. Cushion body 222 can be constructed of a wide variety of resilient materials known in the art and can include, but is not limited to, a thermoplastic or thermoelastic material, including but not limited to an elastomer such as plastic, rubber, silicone, vinyl, foam, or any combination thereof. Cushion body 222 is generally bowl-shaped and is structured to fit over the user's mouth. Cushion body 222 includes a coupling component 224 (FIG. 16), a lower nose engagement portion 226, an inner side 225 and an outer side 227. Cushion body coupling component 224 is structured to be sealingly coupled to faceplate 260, discussed below.

As is known, cushion body 222 is structured to engage the user's face and provides a generally continuous seal over alternate respiratory interface device contour loop 4A (FIG. 1). In an exemplary embodiment, cushion body lower nose engagement portion 226 includes a right side 228, a medial section 229, and a left side 230. As used herein, cushion body lower nose engagement portion lower nose engagement portion right side 228 (hereinafter "lower nose engagement portion right side" 228) and cushion body lower nose engagement portion lower nose engagement portion left side 230 (hereinafter "lower nose engagement portion left side" 230) each includes an inner surface structured to generally correspond to the contour of a user's lower nose right side 12 and lower nose left side 14. Lower nose engagement portion medial section 229 is structured to sealingly engage nose tip 6 and the sides thereof. Further, lower nose engagement portion medial section 229 includes a nose strap 231. Nose strap 231 is, in an exemplary embodiment, a thin member that is structured to be positioned under the user's nose and to engage upper lip 16 or a portion of upper lip 16. Thus, lower nose engagement portion 226 generally corresponds to the shape of a lower portion of a nose, as described above. Other portions of cushion body 222 are structured to be disposed over, i.e. covering as opposed to disposed above, the user's mouth.

Figure 16:
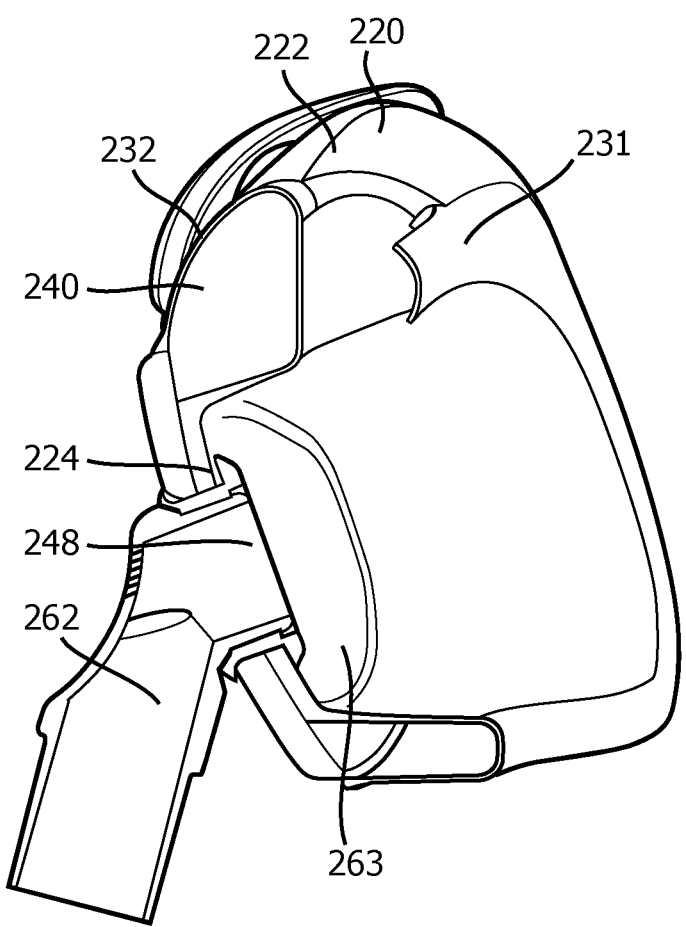
FIG. 16 is a cross-sectional side view of a respiratory interface assembly with the pressure distributing assembly shown in FIG. 14.

In an exemplary embodiment, as shown in FIG. 16 cushion body 222 is an assembly including a thin member 232 and a thick member 240, wherein "thin" and "thick" are terms relative to members 232, 240. Thin member 232 is, in an exemplary embodiment, made from a resilient elastomer such as plastic, rubber, silicone, or vinyl and is a unitary body. Thick member 240 is, in an exemplary embodiment, made from an elastomer foam or a similar material and is a unitary body. In an exemplary embodiment, thick member 240 is resilient, but less resilient than thin member 232. In this embodiment, thin member 232 generally encapsulates thick member 240. That is, both thin member 32 and thick member 240 are generally bowl-shaped with thin member 232 disposed about thick member 240. In an exemplary embodiment, thin member 232 alone defines nose strap 231. Further, cushion body 222, i.e. both thin member 232 and thick member 240, define an inlet passage 248.

In an exemplary embodiment, cushion support assembly 250 includes a faceplate 260 and a pressure distributing assembly 290. In an exemplary embodiment, cushion support assembly faceplate 260 and cushion support assembly pressure distributing assembly 290 are a unitary body. In another exemplary embodiment, cushion support assembly faceplate 260 and cushion support assembly pressure distributing assembly 290 are coupled, directly coupled, or fixed to each other. In this exemplary embodiment, cushion support assembly faceplate 260 (hereinafter "faceplate" 260) is a semi-rigid body 61. That is, faceplate 260 is, in an exemplary embodiment, made from a material that is harder than cushion 220, but which is not as rigid as a hard plastic. In an exemplary embodiment, shown in FIG. 17, faceplate 260 is a single piece, i.e. a unitary body, structured to cover the user's lower nose and mouth. That is, respiratory interface device 10 has a peripheral contour that is, in this embodiment, structured to extend over a user's lower nose and mouth along loop 4A as described above. Faceplate 260 defines lower opening 262. Lower opening 262 can function as a gas inlet. Gas inlet (lower opening 262) can be coupled to a coupling device 264, such as, but not limited to, a swivel conduit, for carrying gas such as air between respiratory interface device 10 and an external gas source, such as a pressure generating system 15, as described above.

Figure 17:
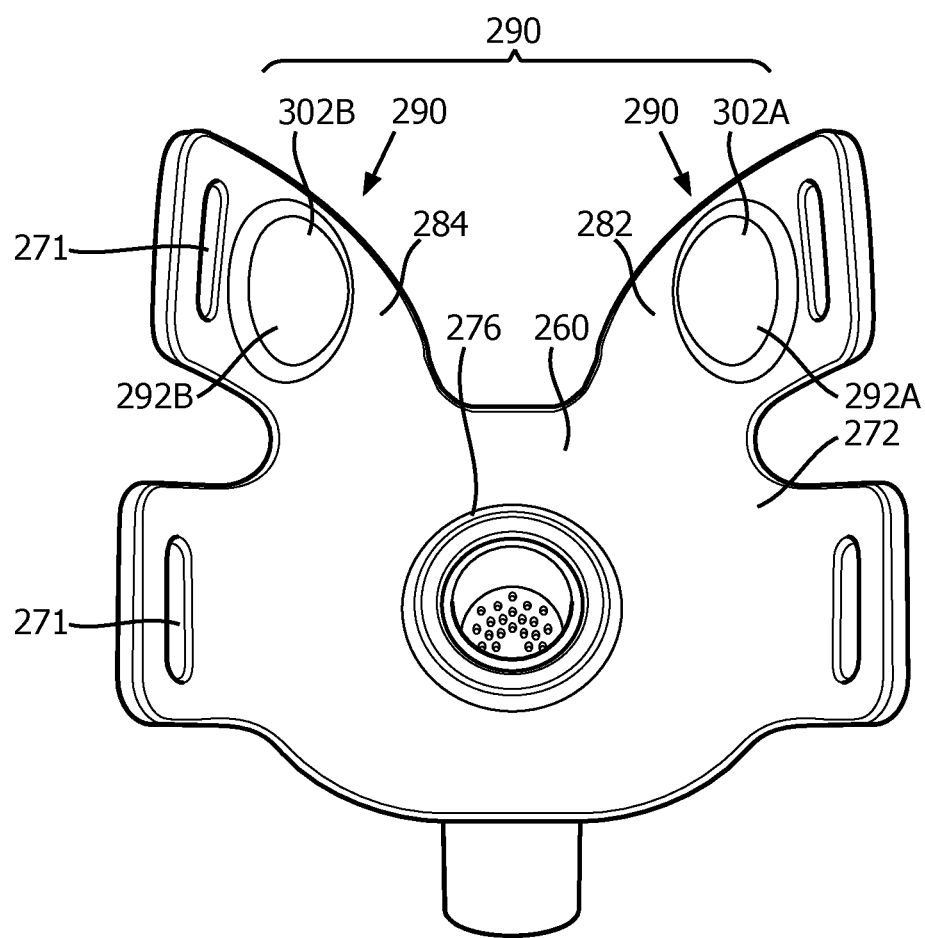
FIG. 17 is a back view of a faceplate of a respiratory interface assembly with the pressure distributing assembly shown in FIG. 14.
Figure 18:
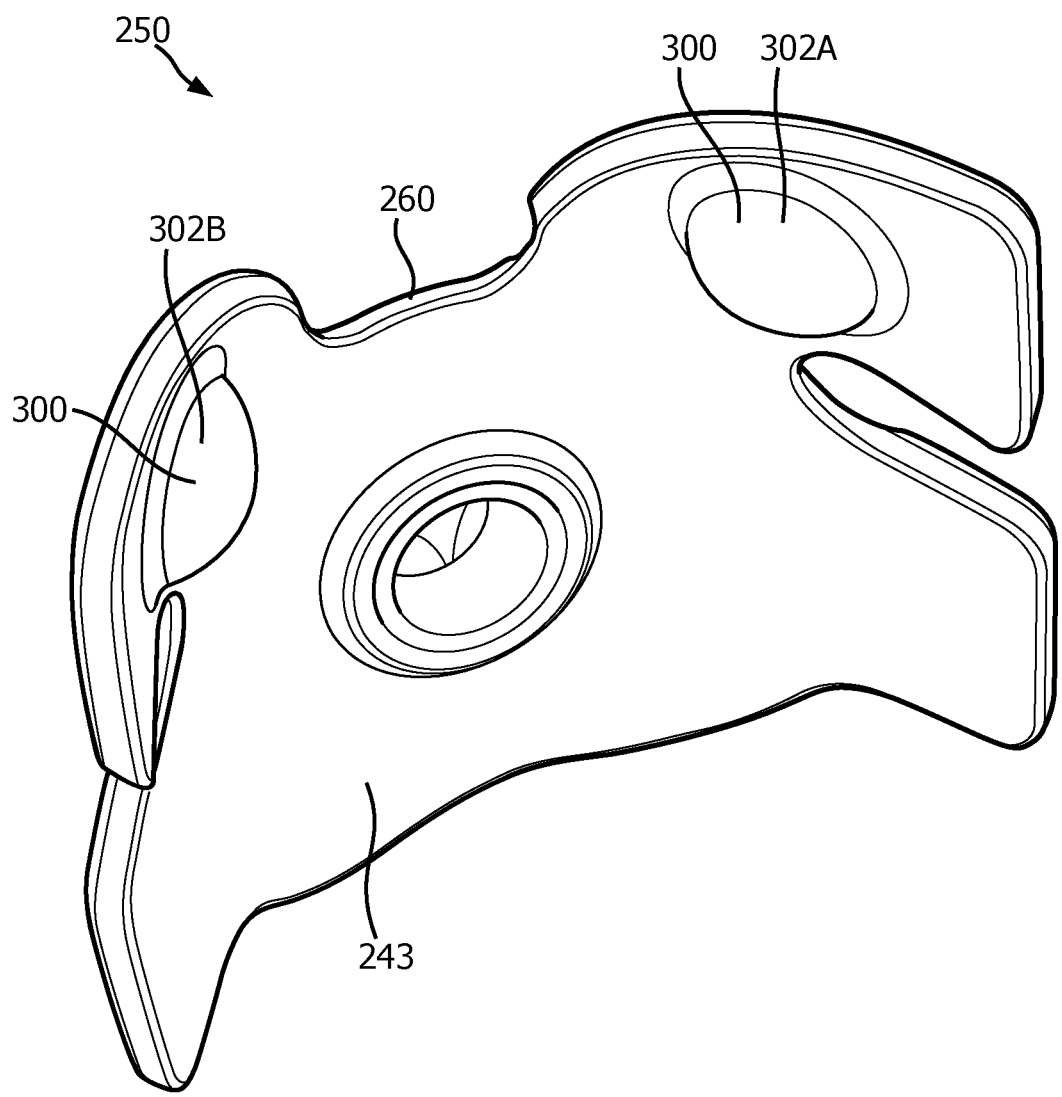
FIG. 18 is an isometric view of a faceplate of a respiratory interface assembly with the pressure distributing assembly shown in FIG. 14.
Figure 19:
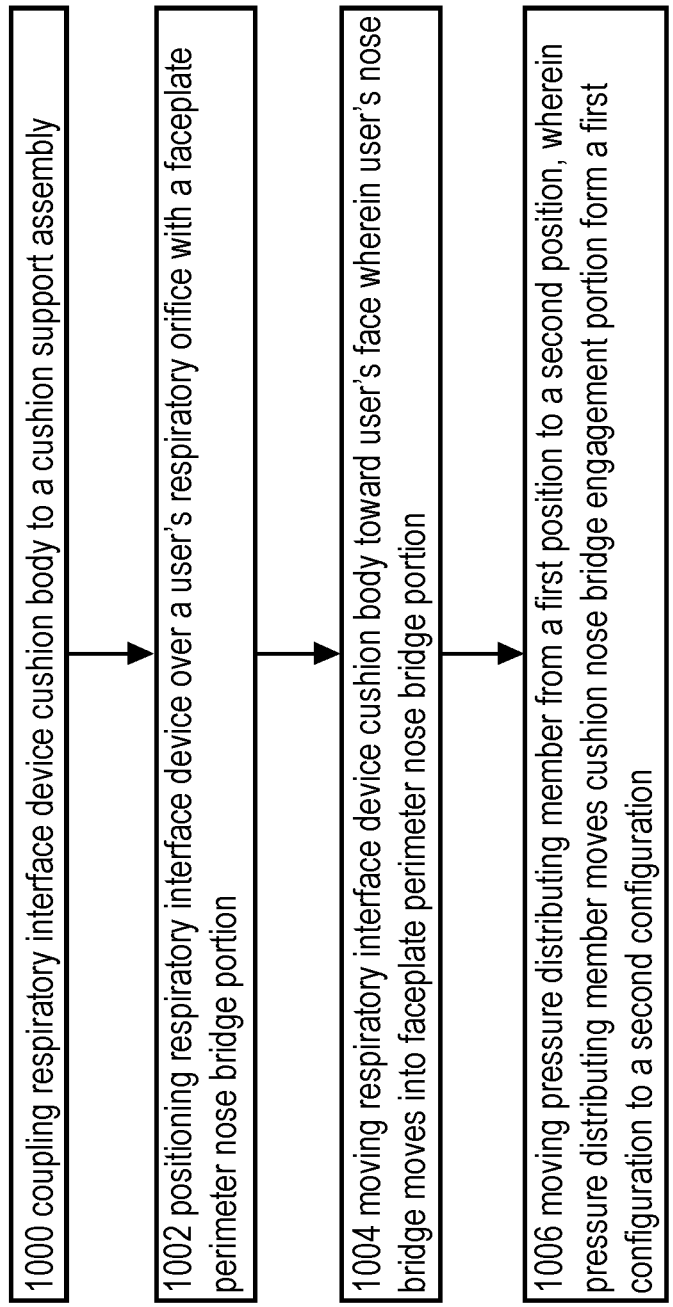
FIG. 19 is a flowchart of the disclosed method.

In an exemplary embodiment, shown in FIGS. 17-18, faceplate 260, i.e. faceplate body 261, is generally convex or bowl-shaped and defines an interior space 263. Faceplate 260 includes an outer side 270, an inner side 272 (relative to the interior space 263). That is, as used herein and with reference to faceplate 260, "outer" or "outwardly" means away from the interior space 263 defined by bowl-shaped faceplate 260, and, "inner" or "inwardly" means toward the interior space 263. In an exemplary embodiment, faceplate 260 includes number of support assembly couplings 271 that are structured to be coupled, including removably coupled, to a support assembly as described above. Faceplate 260 also includes a coupling component 276 structured to be coupled to cushion body coupling component 224. Thus, cushion body 222 is coupled, directly coupled, or removably coupled to faceplate 260. In an exemplary embodiment, faceplate coupling component 276 is a channel disposed about (encircling) faceplate lower opening 262. That is, cushion 220 is coupled to faceplate 260 with cushion body inlet passage 248 aligned with faceplate lower opening 262 and with cushion body coupling component 224 sealingly coupled to faceplate coupling component 276. In an exemplary embodiment, cushion body outer side 227, which is the side immediately adjacent faceplate inner side 272, generally has a smaller cross-sectional area than faceplate inner side 272, as described below.

Figure 15:
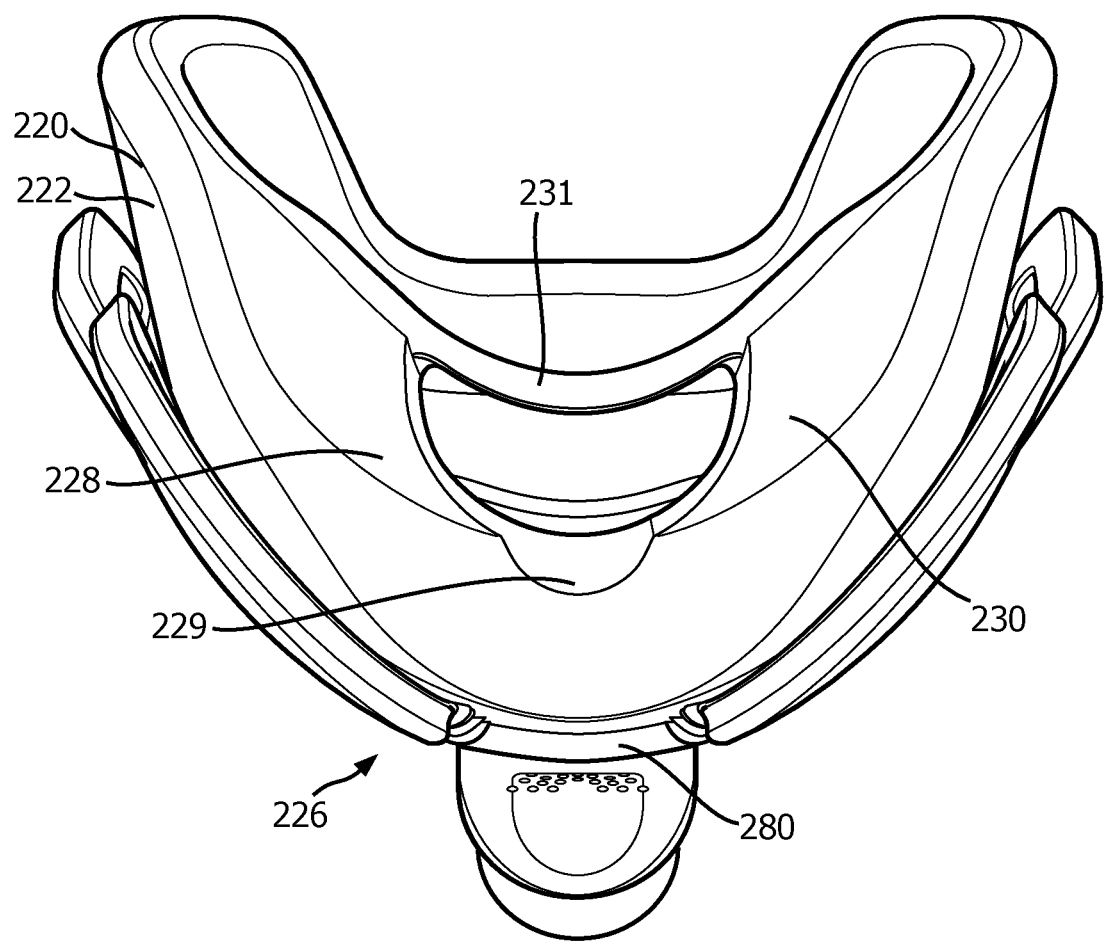
FIG. 15 is a top view of a respiratory interface assembly with the pressure distributing assembly shown in FIG. 14.

Further, in an exemplary embodiment, faceplate 260 includes a lower nose portion 280 that defines an "abutting contour." As used herein, an "abutting contour" is a contour structured to correspond to the surfaces of the lower nose. That is, an "abutting contour" is structured to contact and/or engage the outer sides of the nares, i.e. the lower nose right side 12 and lower nose left side 14, as well as the nose tip 6. An "abutting contour" does not have a substantial length along the Y-axis and, as such, is generally U-shaped. As shown in FIGS. 15 and 17, faceplate lower nose portion 280 is centrally disposed, i.e. disposed on the Y-axis or a centerline of the nose. Thus, faceplate lower nose portion 280 includes a right side 282 and a left side 284.

As noted above, cushion body outer side 227, which is the side immediately adjacent faceplate inner side 272, generally has a smaller cross-sectional area than faceplate inner side 272. In this configuration, cushion 220, i.e. cushion body 222, is generally spaced from faceplate 260. That is, cushion 220 and faceplate 260 are coupled, directly coupled, and/or temporarily coupled at the coupling components 224, 276, but the cushion body outer side 227 is otherwise spaced from faceplate inner side 272. Hereinafter, the space between cushion body outer side 227 and faceplate inner side 272 is identified as "space" 278. In this configuration cushion 220, i.e. cushion body lower nose engagement portion 226, is movable between an un-deformed first configuration and a deformed second configuration, as described below.

Pressure distributing assembly 290 is disposed at faceplate lower nose portion 280. In this exemplary embodiment, pressure distributing assembly 290 is structured to move cushion body lower nose engagement portion 226 between the first configuration and the second configuration, and to maintain cushion body lower nose engagement portion 226 in the second configuration while the respiratory interface device 10 is in use. Pressure distributing assembly 290 includes a number of non-movable pressure distributing members 292. That is, pressure distributing assembly pressure distributing members 292 do not move relative to faceplate 260. Pressure distributing assembly pressure distributing members 292, hereinafter "pressure distributing members" 292, are disposed at faceplate lower nose portion 280.

In an exemplary embodiment, there are two pressure distributing members 292; a first pressure distributing member 292A disposed on faceplate lower nose portion right side 282, and, a second pressure distributing member 292B disposed on faceplate lower nose portion left side 284. Hereinafter, elements of first pressure distributing member 292A will include the letter "A" in the reference number, and, elements of second pressure distributing member 292B will include the letter "B" in the reference number. That is, a generic pressure distributing member 292 will be described with no letters in the reference numbers, but thereafter any reference to a specific pressure distributing member 292, or elements thereof, will include a letter as well. In the configuration described above, first pressure distributing member 292A is structured to, and does, engage lower nose engagement portion right side 228, and, second pressure distributing member 292B is structured to, and does, engage lower nose engagement portion left side 230. That is, first and second pressure distributing members 292A, 292B contact and/or engage an outer side of cushion nose bridge engagement portion right/left sides 228, 230.

In this exemplary embodiment, each pressure distributing member 292 includes a "localized protrusion" 300. As used herein, a "localized protrusion" is a minor portion of a construct, i.e. an area that is smaller than 50% of the construct's surface area, wherein the surface of the construct protrudes relative to the major portion of the construct. The "localized protrusion" may be, but is not limited to, a thickening of the construct (i.e. on a unitary body), or, a smaller element coupled to a larger element. As shown in FIGS. 17-18, each localized protrusion 300 is a "spherical segment" 302. As used herein, a "spherical segment" is a construct having a curved, convex, or arcuate outer surface; a "spherical segment" may be, but does not have to be, generally spherical.

Each spherical segment 302 is coupled, directly coupled, or fixed to faceplate inner side 272. In an exemplary embodiment, each spherical segment 302 is coupled, directly coupled, or fixed to faceplate inner side 272 at faceplate lower nose portion 280. That is, there is a right spherical segment 302A at the faceplate lower nose portion right side 282, and, a left spherical segment 302B disposed on faceplate lower nose portion left side 284. In this configuration, each pressure distributing member 292, i.e. right spherical segment 302A and left spherical segment 302B, effectively narrow the contour of the lower nose portion 280 abutting contour.

In an exemplary embodiment, each pressure distributing member 292, i.e. right spherical segment 302A and left spherical segment 302B, is unitary with faceplate 260 and is made from a semi-rigid material, as is faceplate 260. In another embodiment, each pressure distributing member 292 is unitary with faceplate 260, but is made from a material having a different (greater or lesser) hardness than faceplate 260. In another embodiment, each pressure distributing member 292 is hollow, whereby the surface of each pressure distributing member 292 on faceplate inner side 272 is flexible or compressible.

In this configuration, and when cushion 220 is coupled to faceplate 260 as described above, each pressure distributing member 292 is disposed in space 278. Further, each pressure distributing member 292 contacts cushion body outer side 227. In this configuration, right spherical segment 302A contacts and engages lower nose engagement portion right side 228. That is, the engagement force is a counter-force created when the user tightens respiratory interface device support assembly, i.e. straps as noted above. Similarly, left spherical segment 302B contacts and engages lower nose engagement portion left side 230.

In this exemplary embodiment, pressure distributing assembly 290 is disposed at faceplate lower nose portion 280. Pressure distributing assembly 290 is structured to move cushion body lower nose engagement portion 226 between a first configuration and a second configuration, and to maintain cushion body lower nose engagement portion 226 in the second configuration while the respiratory interface device 10 is in use. That is, as before the use force causes cushion 220 to engage pressure distributing assembly 290 and vice-versa. Thus, when a user positions respiratory interface device 10 for use, i.e. over the user's nose and mouth, cushion 220 is in an un-deformed first configuration wherein right spherical segment 302A merely contacts, or may be spaced from, lower nose engagement portion right side 228. Similarly, left spherical segment 302B merely contacts, or may be spaced from, lower nose engagement portion left side 230. When a user tightens respiratory interface device support assembly, right spherical segment 302A engages lower nose engagement portion right side 228, and, left spherical segment 302B engages lower nose engagement portion left side 230 thereby deforming cushion 220 into a deformed second configuration.

As noted above, and as used herein, a respiratory interface device 10 including a faceplate 260 without a pressure distributing assembly 290 provides a generally continuous seal. Respiratory interface device 10, in this exemplary embodiment, includes pressure distributing assembly 290 and each pressure distributing member 292, i.e. right spherical segment 302A and left spherical segment 302B, cause cushion 220 to provide a more complete seal.

Figure 12:
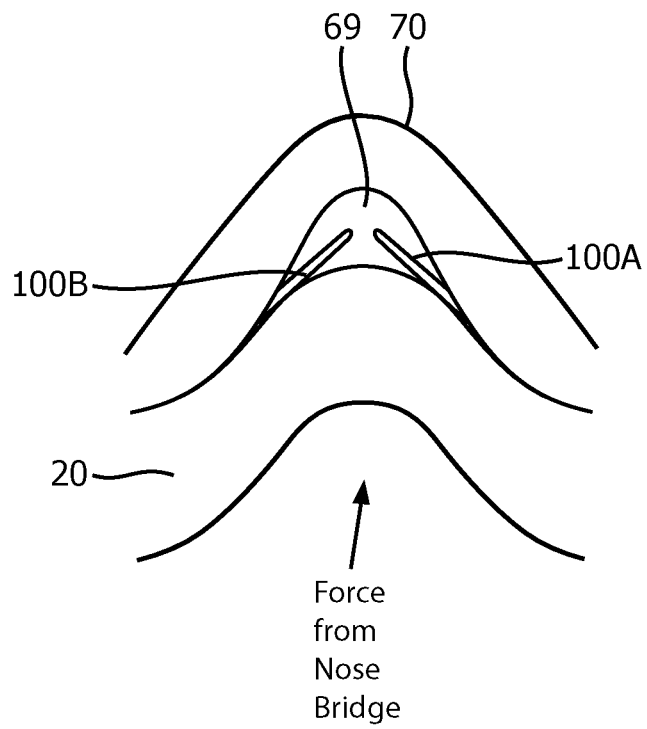
FIG. 12 is a top view of a respiratory interface assembly with a second embodiment of a pressure distributing assembly with the cushion in a first configuration and the pressure distributing members in a first position.
Figure 13:
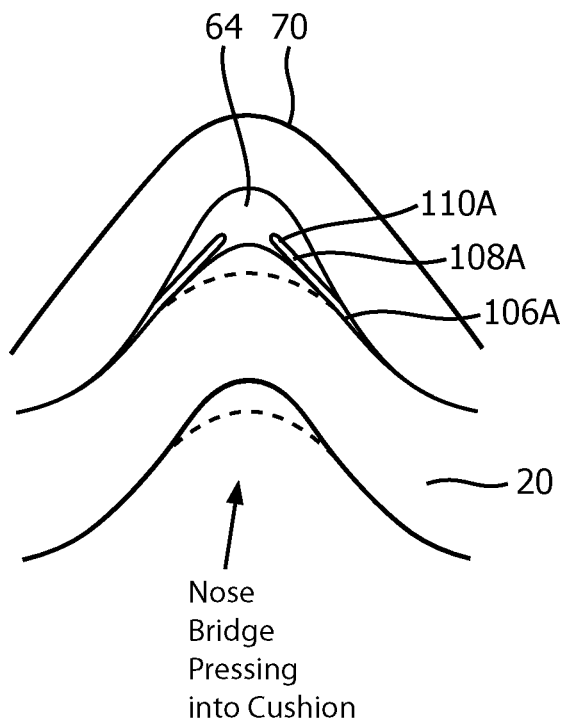
FIG. 13 is a top view of a respiratory interface assembly with a second embodiment of a pressure distributing assembly with the cushion in a second configuration and the pressure distributing members in a second position.
Figure 14:
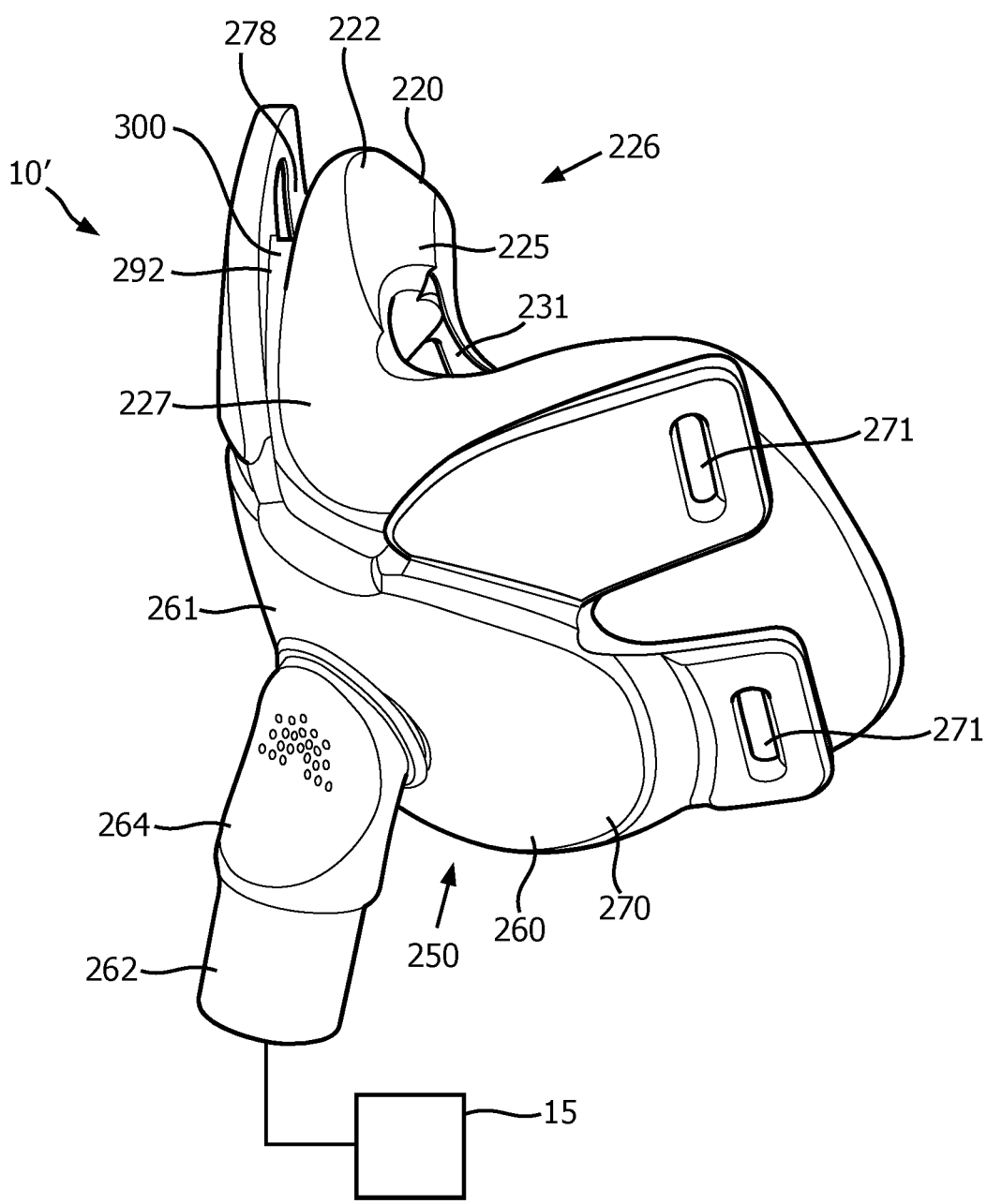
FIG. 14 is an isometric view of a respiratory interface assembly with another embodiment of a pressure distributing assembly.

Accordingly, as shown in FIG. 12, the method of using respiratory interface device 10 described above includes coupling 1000 respiratory interface device cushion body 22 to cushion support assembly 50, positioning 1002 respiratory interface device 10 over a user's respiratory orifice with faceplate perimeter nose bridge portion 80 disposed adjacent the user's nose bridge 5, moving 1004 respiratory interface device cushion body 22 toward user's face wherein user's nose bridge moves into faceplate perimeter nose bridge portion 80, moving 1006 pressure distributing member 92 from a first position to a second position, wherein pressure distributing member 92 moves cushion nose bridge engagement portion 26 from a first configuration to a second configuration.

In the claims, any reference signs placed between parentheses shall not be construed as limiting the claim. The word "comprising" or "including" does not exclude the presence of elements or steps other than those listed in a claim. In a device claim enumerating "several" means, several of these means may be embodied by one and the same item of hardware. The word "a" or "an" preceding an element does not exclude the presence of a plurality of such elements. In any device claim enumerating "several" means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion support assembly for a respiratory interface device cushion, the respiratory interface device cushion including a resilient body including an engagement portion structured to engage a user's nose, the engagement portion being movable between an un-deformed first configuration and a deformed second configuration, the cushion support assembly comprising:

a faceplate including a generally convex body, the faceplate structured to be coupled to the cushion and defining a recessed tapered contour, wherein the faceplate includes a perimeter that includes a nose bridge potion having a right side and a left side, wherein the recessed tapered contour is disposed at the nose bridge portion; and a pressure distributing assembly including a number of pressure distributing members including a first pressure distributing member disposed on a right side of the nose bridge portion and structured to engage a right side of the engagement portion and a second pressure distributing member disposed on a left side of the nose bridge portion and structured to engage a left side of the engagement portion, wherein the first pressure distributing member includes a first elongated body including an inner side, an outer side, a first end, a medial portion, and a second end, wherein the second pressure distributing member includes a second elongated body including an inner side, an outer side, a first end, a medial portion, and a second end, wherein the first elongated body medial portion's inner side engages the engagement portion right side, wherein the second elongated body medial portion's inner side engages the engagement portion left side, wherein the first elongated body medial portion's outer side engages the nose bridge portion right side, wherein the second elongated body medial portion's outer side engages the nose bridge portion left side, wherein the pressure distributing assembly includes a flexure directly coupled to the first elongated body second end and the second elongated body second end, and wherein, when the faceplate is coupled to the cushion, the number of pressure distributing members are structured to maintain the cushion in the un-deformed first configuration, and when a use force is applied to the cushion, the number of pressure distributing members are structured to move and maintain the cushion in the deformed second configuration.

2. A cushion support assembly for a respiratory interface device cushion, the respiratory interface device cushion including a resilient body including an engagement portion structured to engage a user's nose, the engagement portion being movable between an un-deformed first configuration and a deformed second configuration, the cushion support assembly comprising:

a faceplate including a generally convex body, the faceplate structured to be coupled to the cushion and defining recessed tapered contour, wherein the faceplate includes a perimeter that includes a nose bridge portion having a right side and a left side, wherein the recessed tapered contour is disposed at the nose bridge portion; and a pressure distributing assembly including a number of pressure distributing members including a first pressure distributing member disposed on a right side of the nose bridge portion and structured to engage a right side of the engagement portion and a second pressure distributing member disposed on a left side of the nose bridge portion and structured to engage a left side of the engagement portion, wherein the first pressure distributing member includes a first elongated body including an inner side, an outer side, a first end, a medial portion, and a second end, wherein the second pressure distributing member includes a second elongated body including an inner side, an outer side, a first end, a medial portion, and a second end, wherein the first elongated body medial portion's inner side engages the engagement portion right side with a first force, the second elongated body medial portion's inner side engages the engagement portion left side with a second force, the first elongated body first end's inner side engages the engagement portion right side with a third force, and the second elongated body first end's inner side engages the engagement portion left side with a fourth force, wherein the third force is greater than the first force, and the fourth force is greater than the second force, and wherein, when the faceplate is coupled to the cushion, the number of pressure distributing members are structured to maintain the cushion in the un-deformed first configuration, and when a use force is applied to the cushion, the number of pressure distributing members are structured to move and maintain the cushion in the deformed second configuration.

3. The cushion support assembly of claim 1, wherein the pressure distributing assembly freely floats relative to the faceplate.

4. A cushion support assembly for a respiratory interface device cushion, the respiratory interface device cushion including a resilient body including an engagement portion structured to engage a user's nose, the engagement portion being movable between an un-deformed first configuration and a deformed second configuration, the cushion support assembly comprising:

a faceplate including a generally convex body, the faceplate structured to be coupled to the cushion and defining recessed tapered contour, wherein the faceplate includes a perimeter that includes a nose bridge portion having a right side and a left side, wherein the recessed tapered contour is disposed at the nose bridge portion; and a pressure distributing assembly including a number of pressure distributing members including a first pressure distributing member disposed on a right side of the nose bridge portion and structured to engage a right side of the engagement portion and a second pressure distributing member disposed on a left side of the nose bridge portion and structured to engage a left side of the engagement portion, wherein the first pressure distributing member includes a first elongated body including an inner side, an outer side, a first end, a medial portion, and a second end, wherein the second pressure distributing member includes a second elongated body including an inner side, an outer side, a first end, a medial portion, and a second end, wherein the first elongated body medial portion's inner side engages the engagement portion right side, wherein the second elongated body medial portion's inner side engages the engagement portion left side, wherein the first elongated body first end is coupled to the nose bridge portion right side by a first living hinge, wherein the second elongated body first end is coupled to the nose bridge portion left side by a second living hinge, and wherein, when the faceplate is coupled to the cushion, the number of pressure distributing members are structured to maintain the cushion in the un-deformed first configuration, and when a use force is applied to the cushion, the number of pressure distributing members are structured to move and maintain the cushion in the deformed second configuration.

5. The cushion support assembly of claim 1, wherein:

the nose bridge portion defines the tapered contour in both a first lateral plane and a first horizontal plane, wherein a longitudinal axis of the first elongated body is generally disposed in one of a second lateral plane, a second horizontal plane, or is disposed at an angle to both the second lateral plane and the second horizontal plane, and wherein a longitudinal axis of the second elongated body is generally disposed in one of a third lateral plane, a third horizontal plane, or is disposed at an angle to both the third lateral plane and the third horizontal plane.

6. A respiratory interface device comprising:

a respiratory interface device cushion including a resilient body, including an engagement portion structured to engage a user's nose, the engagement portion being movable between an un-deformed first configuration and a deformed second configuration;
a cushion support assembly comprising:
a faceplate including a generally convex body, the faceplate structured to be coupled to the cushion and defining a recessed tapered contour, wherein the faceplate includes a perimeter that includes a nose bridge portion having a right side and a left side, wherein the recessed tapered contour is disposed at the nose bridge portion; and
a pressure distributing assembly including a number of pressure distributing members including a first pressure distributing member disposed on a right side of the nose bridge portion and structured to engage a right side of the engagement portion and a second pressure distributing member disposed on a left side of the nose bridge portion and structured to engage a left side of the engagement portion, wherein the first pressure distributing member includes a first elongated body including an inner side, an outer side, a first end, a medial portion, and a second end,
wherein the second pressure distributing member includes a second elongated body including an inner side, an outer side, a first end, a medial portion, and a second end,
wherein the first elongated body medial portion's inner side engages the engagement portion right side, wherein the second elongated body medial portion's inner side engages the engagement portion left side, wherein the first elongated body medial portion's outer side engages the nose bridge portion right side, wherein the second elongated body medial portion's outer side engages the nose bridge portion left side,
wherein the pressure distributing assembly includes a flexure directly coupled to the first elongated body second end and the second elongated body second end; and wherein, when the faceplate is coupled to the cushion, the number of pressure distributing members are structured to maintain the cushion in the un-deformed first configuration, and when a use force is applied to the cushion, the number of pressure distributing members are structured to move and maintain the cushion in the deformed second configuration.

7. A respiratory interface device, comprising:
a respiratory interface device cushion including a resilient body, including an engagement portion structured to engage a user's nose, the engagement portion being movable between an un-deformed first configuration and a deformed second configuration;
a cushion support assembly comprising:
a faceplate including a generally convex body, the faceplate structured to be coupled to the cushion and defining a recessed tapered contour, wherein the faceplate includes a perimeter that includes a nose bride portion having a right side and a left side, wherein the recessed tapered contour is disposed at the nose bridge portion; and
a pressure distributing assembly including a number of pressure distributing members including a first pressure distributing member disposed on a right side of the nose bridge portion and structured to engage a right side of the engagement portion and a second pressure distributing member disposed on a left side of the nose bridge portion and structured to engage a left side of the engagement portion, wherein the first pressure distributing member includes a first elongated body including an inner side, an outer side, a first end, a medial portion, and a second end,
wherein the second pressure distributing member includes a second elongated body including an inner side, an outer side, a first end, a medial portion, and a second end,
wherein the first elongated body medial portion's inner side engages the engagement portion right side with a first force, the second body medical portion's inner side engages the engagement portion left side with a second force, the first elongated body first end's inner side engages the engagement portion right side with a third force, and the second elongated body first end's inner side engages the engagement portion left side with a fourth force,
wherein the third force is greater than the first force, and the fourth force is greater than the second force, and
wherein, when the faceplate is coupled to the cushion, the number of pressure distributing members are structured to maintain the cushion in the un-deformed first configuration, and when a use force is applied to the cushion, the number of pressure distributing members are structured to move and maintain the cushion in the deformed second configuration.

8. A respiratory interface device, comprising: a respiratory interface device cushion including a resilient body, including an engagement portion structured to engage a user's nose, the engagement portion being movable between an un-deformed first configuration and a deformed second configuration;
a cushion support assembly comprising:
a faceplate including a generally convex body, the faceplate structured to be coupled to the cushion and defining a recessed tapered contour, wherein the faceplate includes a perimeter that includes a nose bridge portion having a right side and a left side, wherein the recessed tapered contour is disposed at the nose bridge portion;
and a pressure distributing assembly including a number of pressure distributing members including a first pressure distributing member disposed on a right side of the nose bridge portion and structured to engage a right side of the engagement portion and a second pressure distributing member disposed on a left side of the nose bridge portion and structured to engage a left side of the engagement portion,
wherein the first pressure distributing member includes a first elongated body including an inner side, an outer side, a first end, a medial portion, and a second end, wherein the second pressure distributing member includes a second elongated body including an inner side, an outer side, a first end, a medial portion, and a second end,
wherein the first elongated body medial portion's inner side engages the engagement portion right side, wherein the second elongated body medial portion's inner side engages the engagement portion left side,
wherein the first elongated body first end is coupled to the nose bridge portion right side by a first living hinge, wherein the second elongated body first end is coupled to the nose bridge portion left side by a second living hinge, and
wherein, when the faceplate is coupled to the cushion, the number of pressure distributing members are structured to maintain the cushion in the un-deformed first configuration, and when a use force is applied to the cushion, the number of pressure distributing members are structured to move and maintain the cushion in the deformed second configuration.

9. A method of using a respiratory interface device comprising:
- a respiratory interface device cushion including a resilient body, including an engagement portion structured to engage a user's nose, the engagement portion being movable between an un-deformed first configuration and a deformed second configuration;
- a cushion support assembly comprising:
  - a faceplate including a generally convex body, the faceplate structured to be coupled to the cushion and defining a recessed tapered contour, wherein the faceplate includes a perimeter that includes a nose bridge portion having a right side and a left side, wherein the recessed tapered contour is disposed at the nose bridge portion; and
  - a pressure distributing assembly including a number of pressure distributing members including a first pressure distributing member disposed on a right side of the nose bridge portion and structured to engage a right side of the engagement portion and a second pressure distributing member disposed on a left side of the nose bridge portion and structured to engage a left side of the engagement portion, wherein the first pressure distributing member includes a first elongated body including an inner side, an outer side, a first end, a medial portion, and a second end, wherein the second pressure distributing member includes a second elongated body including an inner side, an outer side, a first end, a medial portion, and a second end,
- wherein the first elongated body medial portion's inner side engages the engagement portion right side, wherein the second elongated body medial portion's inner side engages the engagement portion left side, wherein the first elongated body medial portion's outer side engages the nose bridge portion right side, wherein the second elongated body medial portion's outer side engages the nose bridge portion left side,
- wherein the pressure distributing assembly includes a flexure directly coupled to the first elongated body second end and the second elongated body second end; and wherein, when the faceplate is coupled to the cushion, the number of pressure distributing members are structured to maintain the cushion in the un-deformed first configuration, and when a use force is applied to the cushion, the number of pressure distributing members are structured to move and maintain the cushion in the deformed second configuration,
- a first position, wherein the number of pressure distributing members maintain the cushion in the un-deformed first configuration, and a second position, wherein the number of pressure distributing members maintain the cushion in the deformed second configuration, the method including:
- coupling the respiratory interface device cushion resilient body to the cushion support assembly;
- positioning the respiratory interface device over a user's respiratory orifice with the nose bridge portion disposed adjacent to the user's nose;
- moving the respiratory interface device cushion body toward the user's face, wherein the user's nose bridge moves into the nose bridge portion; and
- moving the number of pressure distributing members from the first position to the second position, wherein the number of pressure distributing members move the engagement portion from the un-deformed first configuration to the deformed second configuration.

* * * * *